(12) United States Patent
Chase et al.

(10) Patent No.: US 11,160,809 B2
(45) Date of Patent: Nov. 2, 2021

(54) NK1-ANTAGONIST COMBINATION AND METHOD FOR TREATING SYNUCLEINOPATHIES

(71) Applicant: CHASE THERAPEUTICS CORPORATION, Washington, DC (US)

(72) Inventors: Thomas N. Chase, Washington, DC (US); Kathleen E. Clarence-Smith, Washington, DC (US)

(73) Assignee: CHASE THERAPEUTICS CORPORATION, Washington, DC (US)

(*) Notice: Subject to any disclaimer, the term of this patent is extended or adjusted under 35 U.S.C. 154(b) by 4 days.

(21) Appl. No.: 16/604,468

(22) PCT Filed: Apr. 9, 2018

(86) PCT No.: PCT/US2018/026699
§ 371 (c)(1),
(2) Date: Oct. 10, 2019

(87) PCT Pub. No.: WO2018/191160
PCT Pub. Date: Oct. 18, 2018

(65) Prior Publication Data
US 2020/0147097 A1 May 14, 2020

Related U.S. Application Data

(60) Provisional application No. 62/483,555, filed on Apr. 10, 2017.

(51) Int. Cl.
*A61K 31/5377* (2006.01)
*A61K 31/428* (2006.01)
*A61K 31/438* (2006.01)

(52) U.S. Cl.
CPC ........ *A61K 31/5377* (2013.01); *A61K 31/428* (2013.01); *A61K 31/438* (2013.01)

(58) Field of Classification Search
CPC ................ A61K 31/438; A61K 31/445; A61K 31/4747; C07D 401/00; C07D 401/02; C07D 403/04
See application file for complete search history.

(56) References Cited

U.S. PATENT DOCUMENTS

| 2007/0032491 A1 | 2/2007 | Pineiro |
| 2009/0042956 A1 | 2/2009 | Bozik et al. |
| 2009/0221641 A1* | 9/2009 | Janssens ................ A61P 11/16 514/322 |
| 2014/0336158 A1 | 11/2014 | Paliwal et al. |

FOREIGN PATENT DOCUMENTS

| WO | 9824446 A1 | 6/1998 |
| WO | 2019/006050 A1 | 1/2019 |

OTHER PUBLICATIONS

International Search Report for PCT/US2018/026699 dated, Jun. 18, 2018 (PCT/ISA/210).
Written Opinion of the International Searching Authority for PCT/US2018/026699 dated, Jun. 18, 2018 (PCT/ISA/237).
Communication, dated Oct. 29, 2020, issued by the European Patent Office in European Patent Application No. 18 78 5191.
Curran et al., "Aprepitant: A Review of its Use in the Prevention of Nausea and Vomiting," Drugs, 2009, vol. 69, No. 13, pp. 1853-1878.
Samuels, et al., "Comparison of pramipexole with and without domperidone co-administration on alertness, autonomic, and endocrine functions in healthy volunteers," British Journal of Clinical Pharmacology, 2007, vol. 64, No. 5, pp. 591-602.
Chassagnol-Clausade P. et al., "Les medicaments anti-emetiques" Actualites Pharmaceutiques, Elsevier, Amsterdam, NL, vol. 47, No. 477, Sep. 1, 2008 (Sep. 1, 2008), pp. 13-19.
Wood, Lindy D., "Clinical review and treatment of select adverse effects of dopamine receptor agonists in Parkinson's disease," Drugs & Aging, Apr. 1, 2010, vol. 27, No. 4, pp. 295-310.
Communication, dated May 18, 2021, issued by the Eurasian Patent Office in counterpart application No. 201992414.

* cited by examiner

*Primary Examiner* — Deepak R Rao
(74) *Attorney, Agent, or Firm* — Sughrue Mion, PLLC

(57) ABSTRACT

The present invention describes the use of a NK1-antagonist, in combination with 6-propylamino-4,5,6,7-tetrahydro-1,3-benzothiazole-2-amine, to facilitate the treatment of a patient suffering from a synucleinopathy by enabling a therapeutically effective 6-propylamino-4,5,6,7-tetrahydro-1,3-benzothiazole-2-amine daily dose to act without the typical adverse effects caused by pramipexole dihydrochloride monohydrate when administered alone.

23 Claims, No Drawings

NK1-ANTAGONIST COMBINATION AND METHOD FOR TREATING SYNUCLEINOPATHIES

RELATED APPLICATIONS

This application is a National Stage of International Application No. PCT/US2018/026699 filed Apr. 9, 2018, claims the benefit of U.S. Provisional Patent Application Ser. No. 62/483,555, filed Apr. 10, 2017, the disclosures of which are incorporated herein in their entirety by reference.

FIELD OF THE INVENTION

The present invention pertains to the field of the treatment of synucleinopathies, i.e. of neurodegenerative disorders of the human central nervous system, and in particular of the treatment of neurotoxic processes due to the alpha-synuclein oligomerization and aggregation.

OBJECT OF THE INVENTION

The present invention concerns a pharmaceutical combination comprising 6-propylamino-4,5,6,7-tetrahydro-1,3-benzothiazole-2-amine or a pharmaceutically acceptable salt or solvate thereof and an antagonist of the neurokinin receptor subtype-1 ("NK1-antagonist"), including fixed-dose combinations, and its use for the treatment of synucleinopathies, in particular of the CNS neurotoxic effects of alpha-synuclein in a human subject showing an abnormal plasma exosomal/total alpha-synuclein ratio in blood.

Definitions

"CNS": Central Nervous System.
"IR": Immediate Release of the active ingredient from a composition.
"ER": Extended Release of the active ingredient from a composition.
"GI": Gastro-Intestinal.
"AE(s)": Adverse Effect(s).
"SNCA gene": Synuclein-alpha or alpha-synuclein gene.
"MSA": Multiple System Atrophy.
"PD": Parkinson's Disease.
"LBD": Lewy Body Dementia.
"AD": Alzheimer's Disease.
"Synucleinopathy": A disease characterized by the abnormal accumulation, processing, and spreading of alpha-synuclein (α-synuclein) in the brain. Namely, α-synuclein deposits in the central, peripheral, and autonomic nervous system. Synucleinopathies (also called α-synucleinopathies) are neurodegenerative diseases which include, but are not limited to Parkinson's disease, Lewy body dementia (LBD) or dementia with Lewy bodies (DLB), Alzheimer's disease, the Lewy body variant of AD, multiple system atrophy, neurodegeneration with brain iron accumulation, and parkinsonian disorders associated with glucocerebrosidase (GBA) mutations.
"TTS": Transdermal Therapeutic System.
"Effective daily dose of NK1-antagonist": This expression, as used herein, refers to a dose of said NK1-antagonist that is at least as high as that for preventing or treating nausea and vomiting in pediatric or adult patients under cancer chemotherapy according to the current protocols for said treatment. Said daily dose normally is from 1 mg to 600 mg.
"6-Propylamino-4,5,6,7-tetrahydro-1,3-benzothiazole-2-amine": A chiral chemical compound that is available as racemate, chemically (R,S)-6-propylamino-4,5,6,7-tetrahydro-1,3-benzothiazole-2-amine, as (R)-stereoisomer, chemically (R)-6-propylamino-4,5,6,7-tetrahydro-1,3-benzothiazole-2-amine ("dexpramipexole", INN), and as (S)-stereoisomer, chemically (S)-6-propylamino-4,5,6,7-tetrahydro-1,3-benzothiazole-2-amine ("pramipexole", INN). These three chemical entities are basic substances that may be isolated each as an acid addition salt and solvate thereof. Pramipexole dihydrochloride monohydrate is also known with its USAN "pramipexole hydrochloride". As used herein, "6-propylamino-4,5,6,7-tetrahydro-1,3-benzothiazole-2-amine" is a general term that, unless otherwise specified, designates a member selected from the group consisting of pramipexole, the racemate, and a pramipexole/dexpramipexole mixture.
"(R)/(S)-mixture": This term designates a dexpramipexole/pramipexole physical mixture used as an active ingredient according to the present invention.
"(S)-enantiomer": This term, as used herein with reference to 6-propylamino-4,5,6,7-tetrahydro-1,3-benzothiazole-2-amine doses (daily or per unit form) designates the (S)-stereoisomer, included in said doses that, in said 6-propylamino-4,5,6,7-tetrahydro-1,3-benzothiazole-2-amine, are primarily responsible for the dopaminergic action counteracted by the NK1-antagonist. More specifically, S-enantiomer is herein used to designate the S-stereoisomer that is present in the racemate or pharmaceutically acceptable salt thereof, and similarly, to designate the pramipexole or pharmaceutically acceptable salt thereof that is present, as (S)-constituent, in a (R)/(S)-mixture, in order to distinguish it from pramipexole used alone.
The terms "6-propylamino-4,5,6,7-tetrahydro-1,3-benzothiazole-2-amine", "(R)-6-propylamino-4,5,6,7-tetrahydro-1,3-benzothiazole-2-amine", "dexpramipexole", "pramipexole", "(S)-6-propylamino-4,5,6,7-tetrahydro-1,3-benzothiazole-2-amine", "(S)-enantiomer", "racemate" and "(R)/(S)-mixture" include the free bases and pharmaceutically acceptable salts thereof (unless otherwise specified); and the relative doses (daily or per unit form) are given in equivalents of pramipexole dihydrochloride monohydrate.
"Effective daily dose of pramipexole" or "effective daily dose of (S)-enantiomer: An effective pediatric or adult daily pramipexole or pharmaceutically acceptable salts and solvates thereof dose equivalent to at least the pramipexole dihydrochloride monohydrate approved daily dose for the treatment of PD.
"Effective pramipexole amount per unit form" or "effective amount per unit form of (S)-enantiomer": an amount per unit form of pramipexole or pharmaceutically acceptable salt or solvate thereof that is equivalent to at least a pramipexole dihydrochloride monohydrate amount per unit form approved for the treatment of PD. More specifically said amount per unit form is equivalent to from 0.125 mg to 45 mg of pramipexole dihydrochloride monohydrate. As noted above and as used herein, "pramipexole" and "(S)-enantiomer" refer to the same chemical entity, but the term "(S)-enantiomer" is generally used when describing the composition of the racemate and of (R)/(S)-mixtures.

BACKGROUND OF THE INVENTION

Alpha-synuclein, a protein composed of 140 amino acids encoded by the SNCA gene, is abundantly expressed in the human brain and is mainly found in neuronal terminals, especially in the cortex, hippocampus, substantia nigra and cerebellum, where it contributes to the regulation of neurotransmitter release, and is excreted in the blood (Marques and Outeiro, 2012), packaged in exosomes originating from the CNS (Shi et al, 2014).

Under normal circumstances, this soluble protein forms a stably folded tetramer that resists aggregation. But, in certain pathological conditions, for unknown reasons, the alpha-synuclein oligomerizes and aggregates (with the formation of fibrils or "fibrillization"), thus changing its conformation in an abnormal manner into a tertiary, toxic conformation that is also excreted in the blood.

Alpha-synuclein oligomerization and aggregation are thought to be the cause of synucleinopathies, notably PD, LBD, parkinsonian disorders associated with glucocerebrosidase gene (GBA) mutations, MSA, some forms of Alzheimer's disease, and several other disorders, which are collectively referred to as "synucleinopathies". Alpha-synuclein is a ubiquitous protein that is especially abundant in the brain and has been postulated to play a central role in the pathogenesis of Parkinson's disease (PD), Alzheimer's disease, and other neurodegenerative disorders (Kim et al. 2004).

The abnormal plasma exosomal/total alpha-synuclein ratio in the blood of a patient is a diagnostic hallmark of a synucleinopathy.

PD is a common neurodegenerative disorder of the human CNS, first described by James Parkinson in 1817. It has three major clinical signs: resting tremor, bradykinesia, and muscular rigidity. In addition, postural instability and various neurobehavioral disabilities may occur. In the US alone it is estimated that over 1 million individuals are afflicted by this inexorably progressive disorder. Moreover, PD prevalence continues to rise along with the general aging of the American population. Parkinsonian signs are now believed to largely reflect a progressive loss of dopaminergic neurons within the nigrostriatal system. The cause of this degenerative process remains incompletely understood, but now appears to involve the misprocessing of alpha-synuclein into abnormal neurotoxic species.

Dementia with Lewy bodies (Lewy body dementia, LBD) is one of the most common types of progressive dementia. The central features of LBD include progressive cognitive decline, visual hallucinations, and parkinsonian motor symptoms, such as slowness of movement, difficulty walking, and muscular rigidity. Some may also suffer from depression. The symptoms of LBD are caused by the selective loss of nerve cells, presumably a result of synuclein misprocessing and associated with the build-up of Lewy bodies—spherical synuclein accumulations inside many of the degenerating neurons. Researchers do not know why alpha-synuclein accumulates into Lewy bodies or how synuclein species can cause the symptoms of LBD. The formation of LBDs have been considered to be a marker for PD; however, LBDs have also been observed in up to 60% of both sporadic and familial cases of Alzheimer's disease (AD) (Al-Mansoor et al. 2013). Accordingly, the aggregation of α-synuclein has been strongly implicated as a critical step in the development of neurodegenerative diseases (Al-Mansoor et al. 2013).

Sporadic PD or brainstem-predominant type LBD, and dementia with Lewy bodies (DLB) are the two most frequent α-synucleinopathies, and are progressive multisystem neurodegenerative disorders with widespread occurrence of α-synuclein deposits in the central, peripheral, and autonomic nervous system (Jellinger K A 2008a). Reportedly, there is considerable clinical and pathologic overlap between PD (with or without dementia) and DLB (or LBD), corresponding to Braak LB stages 5 and 6, both frequently associated with variable Alzheimer-type pathology (Jellinger K A 2008a). Dementia often does not correlate with progressed stages of LB pathology, but may also be related to concomitant Alzheimer lesions or mixed pathologies (Jellinger K A, 2008a).

Alzheimer disease (AD) has been reported to be featured by deposition of β-amyloid peptides, phosphorylated tau protein (3- and 4-repeat tau) and α-synuclein (aSyn) deposits (Jellinger K A, 2008b). Lewy body diseases (LBD), such as sporadic Parkinson disease (PD) and dementia with Lewy bodies (DLB), show aSyn-positive deposits in neurons, neurites, glia, and presynaptic terminals, while frontotemporal dementias present tau-positive and tau-negative, ubiquitin- and TDP-43-positive neuronal and glial inclusions (Jellinger K A, 2008b). Molecular interactions between major proteins, which may occur within the same brain in various distribution patterns, are associated with various phenotypes and mixed pathologies, e.g. AD with aSyn pathology in the brainstem and amygdala, PD and DLB with AD lesions, and frontotemporal dementia with a mixture of various deposits, while others are featured by one principal pathology without other lesions (e.g. tangle-predominant type of dementia, pure PD, brainstem-predominant LBD) (Jellinger K A, 2008b).

MSA with orthostatic hypotension is the current term for a neurological disorder that was once called Shy-Drager syndrome. A progressive disorder of the central and autonomic nervous systems, it is characterized by orthostatic hypotension (an excessive drop in blood pressure when standing up), which causes dizziness or fainting. Multiple system atrophy can occur without orthostatic hypotension, but instead have urinary tract involvement (urgency/incontinence). Neurologists classify the disorder into 3 types: the Parkinsonian-type includes symptoms of Parkinson's disease such as slow movement, stiff muscles, and tremor; the cerebellar-type, which causes problems with coordination and speech; and the combined-type, which includes symptoms of both parkinsonism and cerebellar failure. Problems with urinary incontinence, constipation, and sexual impotence in men happen early in the course of the disease. Other symptoms include generalized weakness, double vision or other vision disturbances, difficulty breathing and swallowing, sleep disturbances, and decreased sweating. Because the disease resembles others, a correct diagnosis may take years.

Mutations in the glucocerebrosidase gene (GBA) can result in the autosomal recessive disorder Gaucher disease. Different lines of evidence suggest that mutant GBA may be a risk factor for Parkinson's Disease. GBA mutations are now thought to be the single largest risk factor for development of idiopathic PD. Clinically, on imaging, and pharmacologically, GBA PD is almost identical to idiopathic PD (O'Regan et al. 2017). The molecular mechanisms which lead to this increased PD risk in GBA mutation carriers are not fully elucidated, but have been shown to be associated with accumulation of synuclein (Soria et al. 2017).

Several other disorders have also, albeit less frequently, been considered to be synucleinopathies. These include Hallevorden-Spatz syndrome, neuronal axonal dystrophy and some cases of traumatic brain injury. In the case of Hallevorden-Spatz syndrome, symptoms include parkinsonism, dystonia, dysphagia/dysarthria, rigidity/stiffness of limbs, dementia, and spasticity.

Many now believe that processes leading to synuclein aggregation may be central to the neuronal injury and destruction occurring in these disorders.

The mechanism of aggregation in these synucleinopathies remains uncertain. Current evidence suggests the conversion of an alpha helical structure into a beta pleated conformation and subsequent oligomerization might be the pathogenic antecedents to the fibrillization and aggregation of synuclein. These characteristics are similar to the aberrant processing of prion protein that also can become highly neurotoxic. Phosphorylation of alpha-synuclein at the serine-129 residue has been implicated as a contributory factor (Chen et al. 2016). According to this author, a prion form of alpha-synuclein could be a causal agent, especially for multiple system atrophy. Prions are small proteins that also can misfold, oliogomerize, aggregate and propagate to other cells. The result in brain is a profound and spreading neurotoxic process.

Accordingly, inhibiting the misfolding, oligomerization and aggregation of synuclein is beneficial in slowing or even arresting the progression of synucleinopathic disorders.

As mentioned above, alpha-synuclein is readily excreted into extracellular spaces and has been identified in cerebrospinal fluid, blood, and saliva (Marques and Outeiro, 2012). The mechanisms of alpha-synuclein secretion are not fully understood, but studies have demonstrated that at least a fraction of alpha-synuclein is secreted in association with exosomes, the 40 to 100 nm membrane vesicles of endocytic origin (reviewed in Shi et al. 2014). Plasma exosomal alpha-synuclein has been shown to display a significant correlation with disease severity (Shi et al. 2014) meaning that plasma exosomal alpha-synuclein can help monitor disease progression. Similarly, exosomal alpha-synuclein levels correlated with severity of impairment in cross-sectional samples from patients with LBD (Stuendl et al. 2016).

Based on the above, drugs that decrease the plasma exosomal/total alpha-synuclein should slow or even arrest the neurodegenerative process associated with synucleinopathies.

Various compositions for the treatment of PD-associated synucleinopathy and related disorders that target the synuclein aggregation pathway have been proposed. The discovery process primarily involves cellular and animal models of prion and synuclein induced neurodegeneration (Prusiner et al. 2015). Unfortunately, none of these models has been validated and all are deemed relatively uncertain predictors of effects in humans. Nevertheless, these models continue to be widely used in the absence of more reliable discovery techniques.

Pharmaceutical agents currently proposed for consideration include, for instance, such small molecules as (S)-6-propylamino-4,5,6,7-tetrahydro-1,3-benzothiazole-2-amine (pramipexole) and its analogues, alone or in combination with various drugs.

Pramipexole is a synthetic aminothiazole derivative described in U.S. Pat. No. 4,886,812, the contents of which are incorporated herein in their entirety by reference. It is a dopamine autoreceptor agonist (Schneider et al. 1987) of the non-ergoline class that has been approved since the late 1990s for the symptomatic treatment of Parkinson's disease (PD) in doses ranging from 0.375 mg/day to 4.5 mg/day, given in 3 equally divided doses (Mirapex Prescribing Information, July 2016). Pramipexole is supplied in tablets for immediate release containing 0.125 mg, 0.25 mg, 0.5 mg, 1 mg and 1.5 mg of pramipexole dihydrochloride monohydrate; and in tablets for extended release containing 4.5 mg of pramipexole dihydrochloride monohydrate.

Although widely used for the relief of parkinsonian symptoms, its potential as a disease modifying agent has made it the object of considerable investigative attention.

Pramipexole reportedly diminishes synuclein oligomer formation in vitro (Ono et al. 2013). Related studies suggest that pramipexole inhibits the toxic effects of rotenone on dopaminergic neurons in a mouse PD model while reducing immunoreactivity for alpha-synuclein; additionally, pramipexole decreases the in vitro oligomerization of human wild-type alpha-synuclein by $H_2O_2$ plus cytochrome c (Inden et al. 2009). Pramipexole has also been observed to inhibit the aggregation of alpha-synuclein in human neuroblastoma SH-SY5Y cells (Kakimura et al. 2001). Importantly, the relative expression of α-synuclein in serum exosomes has been found to decline during pramipexole treatment of PD-type patients (Luo et al. 2016).

Unfortunately, limitations associated with the administration of pramipexole to synucleinopathic patients complicate its use at the potentially higher neuroprotective doses predicted by some animal models. First, mechanisms to explain its putatively beneficial effects on synuclein-related neurotoxicity continue to elude full understanding. Second, effect sizes in animal model studies tend to be small and occur only at relatively high drug doses. Both situations were also observed in the above mentioned report of pramipexole-induced changes in exosomal synuclein in PD patients, which were associated with the administration of the highest—4.5 mg/day—recommended/approved dose of pramipexole (Mirapex Package Insert; Revised July 2016).

In the report by Luo et al. (2016), although treatment of Parkinson patients with pramipexole, at therapeutic doses approved for the treatment of the motor symptoms of PD, significantly lowered the relative expression of alpha-synuclein (compared with pre-treatment values), the magnitude of the effect was small. Higher doses of pramipexole could have been more efficacious, but side effects such as vomiting and severe nausea preclude the use of higher doses. For example, Corrigan et al (2000) report that doses of 5 mg/day of pramipexole, hardly higher than the maximum recommended dose of 4.5 mg/day (Pramipexole FDA-approved package Insert) caused nausea in 76% of patients and vomiting in 39% of patients. Furthermore, 36% of patients were not able to complete the study, presumably because of intolerable GI adverse events.

Recently, it began to be reported that pramipexole can exert neuroprotective effects in various in vitro cellular and in vivo animal models of PD. Mechanisms by which these protective effects may occur remain uncertain. Unfortunately, the protective effects of pramipexole in animal models are generally small and require higher doses than considered safe and tolerable for human administration. It is thus hardly surprising that pramipexole, in doses approved for the treatment of motor symptoms of PD failed to evidence neuroprotective (i.e., disease modifying) activity in a randomized, controlled, clinical trial involving 535 PD patients (Schapira et al. 2013).

(R)/(S)-mixtures, consisting of pharmaceutical compositions comprising a therapeutically effective amount of dexpramipexole or pharmaceutically acceptable salts and solvates thereof and a therapeutically effective amount of pramipexole or pharmaceutically acceptable salts and solvates thereof, useful for the treatment of PD, are disclosed in US 2008/0014259, the contents of which are incorporated herein in their entirety by reference.

According to US 2008/0014259, both enantiomers are able to confer neuroprotective effects by their ability to accumulate in brain cells, the spinal cord and mitochondria where they exert a positive effect on neurological function that is independent of the dopamine agonist activity of pramipexole. In particular, said document proposes said composition as a neuroprotective agent and a therapeutically effective amount of from about 0.0625 mg to about 6 mg of pramipexole in combination with up to 5000 mg of dexpramipexole. However, this document emphasizes the pramipexole adverse effects due to its dopaminergic action and tends to favor pramipexole low doses, as also confirmed by the same applicant in the almost concurrent WO 2008/113003, the contents of which are incorporated herein in their entirety by reference.

According to US 2013/0116292, the contents of which are incorporated herein in their entirety by reference, dexpramipexole, or pharmaceutically acceptable salts and solvates thereof, acts by slowing the progression of neuronal degeneration and/or by preventing neuronal cell death. However, no further mention of this possible noteworthy action of dexpramipexole appeared in the literature.

A synthesis of dexpramipexole and of pharmaceutically acceptable salts thereof, in particular dexpramipexole dihydrochloride monohydrate, is described in US 2012/0253047, the contents of which are incorporated herein in their entirety by reference.

Notwithstanding the massive existing literature, pramipexole continues to provide only marginal activity in the treatment of Parkinson's disease.

Thus, the problem of providing safe, chronic, effective treatment of a patient suffering from a synucleinopathy with pramipexole remains unsolved.

SUMMARY OF THE INVENTION

The present invention derives from the idea that increasing the therapeutic window for pramipexole, when given also with neuroprotective intent might safely enable its full efficacy to a degree that delays onset and/or slows symptom progression to a clinically significant extent in those with PD-like disorders.

The present invention shows that increasing the tolerable dosages of pramipexole to unexpected levels, safely enable its full efficacy to a degree that delays onset and/or slows symptom progression to a clinically significant extent in those with PD-like disorders.

It has now been found that pharmaceuticals such as aprepitant, netupitant, and rolapitant, by reducing or even abrogating the GI side effects, in particular nausea and vomiting, of high doses of pramipexole enables the synucleinopathy-modifying potential of pramipexole.

It has also been found that, by using a NK1 receptor antagonist, also referred to as NK1 receptor inhibitor or simply NK1-antagonist, in combination with pramipexole or a pharmaceutically acceptable salt or solvate thereof, it is possible to treat a patient suffering from a synucleinopathy by maintaining a therapeutically effective pramipexole or pharmaceutically acceptable salt or solvate thereof daily dose with minimal adverse effect.

In addition, it has been found that said NK1-antagonist allows the safe administration of 6-propylamino-4,5,6,7-tetrahydro-1,3-benzothiazole-2-amine at a daily dose comprising a (S)-enantiomer dose that may be higher, and even much higher, than the pramipexole maximum daily dose recommended for the relief of the motor symptoms of Parkinson's disease. Consequently, an improvement of the conditions of a patient suffering from a synucleinopathy, in particular PD, Lewy body disease, parkinsonian disorders associated with glucocerebrosidase (GBA) mutations, and MSA is attained.

The combination of a NK1-antagonist, such as aprepitant, rolapitant, or netupitant, as Component (a), with 6-propylamino-4,5,6,7-tetrahydro-1,3-benzothiazole-2-amine, as Component (b), acts in a way that leads to normalizing the abnormal ratio of monomeric to oligomeric synuclein species in plasma exosomes originating from the CNS of patients suffering from a synucleinopathy.

Thus, the present invention provides a NK1-antagonist, for use for the treatment of synucleinopathies in a patient in need of said treatment, in combination with a 6-propylamino-4,5,6,7-tetrahydro-1,3-benzothiazole-2-amine. Said combination acts in a way that tends to normalize the abnormal ratio of monomeric to oligomeric synuclein species in plasma exosomes originating from the CNS.

The invention also provides a method for treating a patient suffering from a synucleinopathy which comprises treating said patient with an effective dose of a NK1-antagonist in combination with a 6-propylamino-4,5,6,7-tetrahydro-1,3-benzothiazole-2-amine.

According to an embodiment, said NK1-antagonist and said 6-propylamino-4,5,6,7-tetrahydro-1,3-benzothiazole-2-amine are each formulated in a pharmaceutical composition in admixture with a pharmaceutical carrier and separately administered to the patient in need of treatment with said combination.

According to another embodiment, said NK1-antagonist and said 6-propylamino-4,5,6,7-tetrahydro-1,3-benzothiazole-2-amine are mixed together and formulated in a pharmaceutical composition (fixed-dose combination), in admixture with a pharmaceutical carrier, to be administered to the patient in need of said treatment.

Any of the NK1-antagonists that is effective for preventing nausea and vomiting may be used in combination with a dose of 6-propylamino-4,5,6,7-tetrahydro-1,3-benzothiazole-2-amine including a (S)-enantiomer dose that is generally currently used for treating PD, or with a higher, and even at a much higher dose. Numerous suitable NK1-antagonists are disclosed in the literature. The chronic use of this combination improves the symptoms of a synucleinopathy by concurrently mitigating or even eliminating the adverse effects induced by said 6-propylamino-4,5,6,7-tetrahydro-1,3-benzothiazole-2-amine alone.

As stated in the definitions, 6-propylamino-4,5,6,7-tetrahydro-1,3-benzothiazole-2-amine stands for the active principle per se, independently of the salt or solvate of said active principle. Similarly, the expressions "salts or solvates thereof" and "salts and solvates thereof", in reference to any of the cited NK1-antagonists or to 6-propylamino-4,5,6,7-tetrahydro-1,3-benzothiazole-2-amine, indicates that the salt of any of said cited NK1-antagonists or of said 6-propylamino-4,5,6,7-tetrahydro-1,3-benzothiazole-2-amine may be solvated with a solvent, normally water.

According to the present invention, preferably, the NK1-antagonists used are those approved for preventing nausea and vomiting following cancer chemotherapy. In fact, surprisingly, NK1 receptor inhibitors, known to block nausea, vomiting, and diarrhea induced by chemotherapeutic drugs, have been shown to also block the gastro-intestinal side effects of the (S)-enantiomer contained in said 6-propylamino-4,5,6,7-tetrahydro-1,3-benzothiazole-2-amine without affecting its efficacy in treating said synucleinopathy.

This finding is surprising also because both the NK1-antagonists and the 6-propylamino-4,5,6,7-tetrahydro-1,3- benzothiazole-2-amine are two families of products that have been in use for more than a decade, each for its own indications, but no one has thought to combine them for the treatment of synucleinopathies. In particular, to date, no one has suggested that, by combining an effective dose of NK1-antagonist with an effective anti-synucleinopathy dose of 6-propylamino-4,5,6,7-tetrahydro-1,3-benzothiazole-2-amine, it would be possible to safely improve the conditions of patients suffering from a synucleinopathy. In addition, no one suspected that, in the case of pramipexole, such a combination would normally allow the administration of the maximal recommended daily dose of said pramipexole and even to allow a possible increase of the dose of pramipexole dihydrochloride monohydrate.

More particularly, it has been found that, in the case of pramipexole dihydrochloride monohydrate, its combination with a NK1-antagonist allows the administration of a therapeutic effective anti-synucleinopathic dose that, in many patients, will significantly exceed the maximum recommended dose (4.5 mg/day) of pramipexole dihydrochloride monohydrate for the treatment of the motor symptoms of PD, thus increasing its efficacy in the treatment of a patient suffering from a synucleinopathy such as PD, including unexpectedly and substantially slowing disease progression.

Thus, the present invention provides a method for treating a synucleinopathy, which comprises administering to a patient in need of said treatment an effective daily dose of a NK1-antagonist in combination with an effective daily dose of a 6-propylamino-4,5,6,7-tetrahydro-1,3-benzothiazole-2-amine.

Pharmaceutically acceptable salts of 6-propylamino-4,5,6,7-tetrahydro-1,3-benzothiazole-2-amine are also included in the present invention.

According to an embodiment, the invention provides a pharmaceutical combination comprising a NK1-antagonist, normally at a daily dose that is at least as high as the dose approved for the prevention or treatment of postoperative nausea and vomiting or for the prevention of chemotherapy-induced nausea and vomiting, and an effective daily dose of a 6-propylamino-4,5,6,7-tetrahydro-1,3-benzothiazole-2-amine.

More particularly, according to this embodiment, said 6-propylamino-4,5,6,7-tetrahydro-1,3-benzothiazole-2-amine is pramipexole or a pharmaceutically acceptable salt or solvate thereof, for its use in the treatment of a synucleinopathy in a patient in need of said treatment, is administered at a daily dose equivalent to from 0.375 mg to 45 mg of pramipexole dihydrochloride monohydrate.

According to another embodiment, the invention provides a NK1-antagonist, in a pharmaceutical composition Component (a) comprising, as an active ingredient, said NK1-antagonist in admixture with a pharmaceutical carrier or vehicle, to be administered in combination with 6-propylamino-4,5,6,7-tetrahydro-1,3-benzothiazole-2-amine, also in a pharmaceutical composition Component (b), in admixture with a pharmaceutical carrier or vehicle.

The amount of NK1-antagonist/unit form in said composition is from 1 µg to 600 mg, normally from 1 mg to 600 mg, and the amount of 6-propylamino-4,5,6,7-tetrahydro-1,3-benzothiazole-2-amine/unit form in said composition is from 0.125 mg to 3000 mg.

According to this embodiment, said NK1-antagonist is preferably present in said composition, in an amount per unit form at least as high as the dose per unit form approved for the prevention or treatment of postoperative nausea and vomiting or for the prevention of chemotherapy-induced nausea and vomiting, in admixture with a pharmaceutical carrier, for use for preventing or curing the adverse effects of pramipexole, administered in a pharmaceutically composition comprising said pramipexole, or a pharmaceutically acceptable salt thereof, in an amount per unit form equivalent to from 0.125 mg to 45 mg, preferably from 0.125 mg to 40-42 mg of pramipexole dihydrochloride monohydrate, in the treatment of synucleinopathies.

According to another aspect of this embodiment, the invention provides a pharmaceutical combination comprising
(a) a NK1-antagonist, in a pharmaceutical composition comprising, as an active ingredient, said NK1-antagonist, in an amount at least as high as the dose/unit form approved for the prevention or treatment of postoperative nausea and vomiting or for the prevention of chemotherapy-induced nausea and vomiting, in admixture with a pharmaceutical carrier or vehicle; and
(b) pramipexole dihydrochloride monohydrate, in a pharmaceutical composition comprising, as an active ingredient, said pramipexole dihydrochloride monohydrate, in an amount per unit form at least as high as the dose/unit form approved for the treatment of Parkinson's disease, in admixture with a pharmaceutical carrier or vehicle.

In said combination, Component (a) is present in said composition in an amount of from 1 µg to 600 mg, normally from 1 mg to 600 mg or from 1 mg to 300 mg, and component (b) is present, as pramipexole dihydrochloride monohydrate, in an amount of from 0.125 mg to 45 mg, preferably from 0.125 mg to 40-42 mg, normally from 0.125 mg to 20-21 mg.

According to a further embodiment, the invention provides the use of a NK1-antagonist for the preparation of a medicament consisting of a pharmaceutical composition comprising, as an active ingredient, said NK1-antagonist, in an amount per unit form at least as high as the dose approved for the prevention or treatment of postoperative nausea and vomiting or for the prevention of chemotherapy-induced nausea and vomiting, in admixture with a pharmaceutical carrier, for preventing or curing the adverse effects of 6-propylamino-4,5,6,7-tetrahydro-1,3-benzothiazole-2-amine or of a pharmaceutically acceptable salt and/or solvate thereof, in the treatment of a synucleinopathy.

As set forth above, the amount per unit form of the NK1-antagonist is at least as high as the dose approved for the prevention or treatment of postoperative nausea and vomiting or for the prevention of chemotherapy-induced nausea and vomiting and may be up to 6 times said dose or greater, and the amount/unit form of 6-propylamino-4,5,6,7-tetrahydro-1,3-benzothiazole-2-amine is from 0.125 mg to 3000 mg.

According to yet a further embodiment, the invention provides a pharmaceutical fixed-dose combination consisting of a pharmaceutical composition comprising an effective dose per unit form of a NK1-antagonist, as Component (a) and an effective dose per unit form of a 6-propylamino-4,5,6,7-tetrahydro-1,3-benzothiazole-2-amine, as Component (b), in admixture with a pharmaceutical carrier or vehicle.

The amount of the 6-propylamino-4,5,6,7-tetrahydro-1,3-benzothiazole-2-amine per IR-unit form will be in a range equivalent to from 0.125 mg to 1500 mg of pramipexole dihydrochloride monohydrate, depending on safety and tolerability (in combination with the NK1-antagonist).

Normally, if said 6-propylamino-4,5,6,7-tetrahydro-1,3-benzothiazole-2-amine is pramipexole dihydrochloride monohydrate in IR formulation, the dose-range is from 0.125 mg to 30 mg, preferably from 0.125 mg to 22.5 mg, normally from 0.125 mg to 20 mg or from 0.125 mg to 10 mg, per unit form, depending on safety and tolerability (in combination with the NK1-antagonist).

The dose/unit form of 6-propylamino-4,5,6,7-tetrahydro-1,3-benzothiazole-2-amine in an ER formulation, including slow-release compositions and transdermal therapeutic systems such as transdermal patches, will range from 1.5 mg to 3000 mg, depending on the tolerability (in combination with the NK1-antagonist). Normally, if said 6-propylamino-4,5,6,7-tetrahydro-1,3-benzothiazole-2-amine is pramipexole dihydrochloride monohydrate, the dose-range/unit form will be from 1.5 mg to 45 mg, preferably from 1.5 mg to 40-42 mg, or 3 mg to 40-42 mg, normally from 3 mg to 20-21 mg.

The dose of the 6-propylamino-4,5,6,7-tetrahydro-1,3-benzothiazole-2-amine, as a (R)/(S)-mixture, per IR-unit form will range from 50 mg to 1500 mg, depending on safety and tolerability (in combination with the NK1-antagonist). The above range is inclusive of a (S)-enantiomer amount of from 0.125 mg to 10 mg per IR-unit form. For the administration of pramipexole at higher doses, the above range will be from 0.125 mg to 22.5 mg, normally from 0.125 mg to 20 mg, advantageously from 6.5 mg to 20 mg per IR-unit form.

Normally, if said 6-propylamino-4,5,6,7-tetrahydro-1,3-benzothiazole-2-amine is pramipexole dihydrochloride monohydrate, the dose-range is from 0.125 mg to 10 mg, advantageously from 1.5 mg to 10 mg or from 6.5 mg to 10 mg per IR-unit form, depending on safety and tolerability (in combination with the NK1-antagonist). For the administration of pramipexole at higher doses, said dose-range will be from 0.125 mg to 20 mg, normally from 6.5 mg to 20 mg.

The dose/unit form of 6-propylamino-4,5,6,7-tetrahydro-1,3-benzothiazole-2-amine in an ER formulation, including slow-release compositions and transdermal therapeutic systems such as transdermal patches, will range from 3 mg to 3000 mg, depending on the tolerability (in combination with the NK1-antagonist).

The dose/unit form of 6-propylamino-4,5,6,7-tetrahydro-1,3-benzothiazole-2-amine, as a (R)/(S)-mixture, in an ER formulation, including slow-release compositions and transdermal therapeutic systems such as transdermal patches, will be in a range from 150 mg to 3000 mg. normally from 300 mg to 3000 mg of pramipexole dihydrochloride monohydrate, inclusive of a (S)-enantiomer dose/unit form equivalent to from 0.375 mg to 45 mg, normally from 0.375 mg to 40-42 mg, or from more than 6 mg to 40-42 mg of pramipexole dihydrochloride monohydrate; preferably, from 0.375 mg to 40-42 mg, or from more than 6 mg to 40-42 mg of pramipexole dihydrochloride monohydrate, depending on the tolerability (in combination with the NK1-antagonist).

Normally, if said 6-propylamino-4,5,6,7-tetrahydro-1,3-benzothiazole-2-amine is pramipexole dihydrochloride monohydrate, the dose-range/ER-unit form will be from 3 mg to 45 mg. Advantageously, if said 6-propylamino-4,5,6,7-tetrahydro-1,3-benzothiazole-2-amine is pramipexole or a pharmaceutically acceptable salt thereof, said dose-range/ER-unit form will be equivalent to from more than 4.5 mg to 45 mg or from more than 6 mg to 45 mg, preferably, preferably from more than 4.5 mg to 40-42 mg or from more than 6 mg to 40-42 mg, in some cases from more than 4.5 mg to 22.5 mg, preferably from more than 6 mg to 20 mg or from 6.5 mg to 20 mg, of pramipexole dihydrochloride monohydrate. Preferably, said dose-range/ER-unit form will be equivalent to from more than 4.5 mg to 40-42 mg or from more than 6 mg to 40-42 mg, in some cases from more than 4.5 mg to 20 mg, preferably from more than 6 mg to 20 mg or from 6.5 mg to 20 mg, of pramipexole dihydrochloride monohydrate.

If the NK1-antagonist is aprepitant, said aprepitant will be in an IR dose ranging from 10 mg to 250 mg, or in some embodiments from 10 mg to 125 mg.

If the NK1-antagonist is fosaprepitant or a pharmaceutically acceptable salt or solvate thereof, said NK1-antagonist will be in an IR dose equivalent to from 10 mg to 250 mg of aprepitant.

If the NK1-antagonist is rolapitant, the dose per unit form in combination with 6-propylamino-4,5,6,7-tetrahydro-1,3-benzothiazole-2-amine, at the above doses/unit form, will range from 15 mg to 270 mg in an IR formulation.

Normally, in the method (or use) for the treatment of a synucleinopathy according to the present invention (in combination with a NK1-antagonist), the 6-propylamino-4,5,6,7-tetrahydro-1,3-benzothiazole-2-amine, normally in a pharmaceutical composition in admixture with a pharmaceutical carrier or vehicle, is administered to a patient in need of said treatment at a daily dose of from 1.5 mg to 3000 mg. In practice, said daily dose is selected from the group consisting of pramipexole or a pharmaceutically acceptable salt thereof, at a daily dose equivalent to from 1.5 mg to 45 mg of pramipexole dihydrochloride monohydrate;

the racemate or a pharmaceutically acceptable salt thereof, at a daily dose of from 3 mg to 90 mg of pramipexole dihydrochloride monohydrate (thus, obviously, including a daily dose of (S)-6-propylamino-4,5,6,7-tetrahydro-1,3-benzothiazole-2-amine equivalent to from 1.5 mg to 45 mg of pramipexole dihydrochloride monohydrate, and a daily dose of (R)-6-propylamino-4,5,6,7-tetrahydro-1,3-benzothiazole-2-amine equivalent to from 1.5 mg to 45 mg of pramipexole dihydrochloride monohydrate); and a (R)/(S)-mixture, at a daily dose of from 150 mg to 3000 mg, including a (S)-enantiomer daily dose equivalent to from 1.5 mg to 45 mg, preferably from 1.5 mg to 40-42 mg of pramipexole dihydrochloride monohydrate (thus, obviously, said daily dose being constituted by a dose of (S)-enantiomer equivalent to from 1.5 mg to 45 mg, preferably from 1.5 mg to 40-42 mg of pramipexole dihydrochloride monohydrate and by a (R)-6-propylamino-4,5,6,7-tetrahydro-1,3-benzothiazole-2-amine dose equivalent to from 150 mg to 3000 mg (minus from 1.5 mg to 45 mg, preferably from 1.5 to 40-42 mg) of pramipexole dihydrochloride monohydrate).

In the method (or use) for the treatment of a synucleinopathy according to the present invention, the 6-propylamino-4,5,6,7-tetrahydro-1,3-benzothiazole-2-amine, as a (R)/(S)-mixture, normally in a pharmaceutical composition in admixture with a pharmaceutical carrier or vehicle, is administered to a patient in need of said treatment at a daily dose of from 1.5 mg to 3000 mg or of from 3.0 mg to 3000 mg; inclusive of a (S)-enantiomer daily dose equivalent to from 0.375 mg to 45 mg, preferably inclusive of a (S)-enantiomer daily dose of from more than 6 mg to 45 mg or from 6.5 mg to 45 mg of pramipexole dihydrochloride monohydrate, and more preferably, inclusive of a (S)-enantiomer daily dose equivalent to from 0.375 mg to 40-42 mg, of from more than 6 mg to 40-42 mg or of from 6.5 mg to 40-42 mg of pramipexole dihydrochloride monohydrate.

According to a particular embodiment, in said method (or use), said 6-propylamino-4,5,6,7-tetrahydro-1,3-benzothiazole-2-amine is pramipexole dihydrochloride monohydrate that is administered to said patient at a daily dose of from 1.5 mg to 45 mg, preferably from 1.5 mg to 40-42 mg, normally from 1.5 mg to 20 mg. According to this embodiment, in said method (or use) the 6-propylamino-4,5,6,7-tetrahydro-1,3-benzothiazole-2-amine is administered to said patient in combination with a NK1-antagonist.

If the NK1-antagonist is aprepitant or fosaprepitant, said NK1-antagonist is administered to said patient at a daily dose, in aprepitant, of from 10 mg to 250 mg, or in some embodiments of from 10 mg to 125 mg.

If the NK1-antagonist is rolapitant, said rolapitant is administered to said patient at a daily dose of from 15 mg to 270 mg.

DETAILED DESCRIPTION

As summarized above, the present invention provides a combination, including fixed-dose combinations, of a NK1-antagonist Component (a) with 6-propylamino-4,5,6,7-tetrahydro-1,3-benzothiazole-2-amine Component (b), and its use for the treatment of a synucleinopathy in a patient. In particular, the invention provides
- a method for treating a patient suffering from a synucleinopathy which comprises treating said patient with a NK1-antagonist in combination with 6-propylamino-4,5,6,7-tetrahydro-1,3-benzothiazole-2-amine Component (b);
- a NK1-antagonist Component (a), for use in combination with 6-propylamino-4,5,6,7-tetrahydro-1,3-benzothiazole-2-amine Component (b) in the treatment of a patient suffering from a synucleinopathy;
- the use of a NK1-antagonist for the preparation of a medicament for treating a synucleinopathy in a patient in need of said treatment, in combination with 6-propylamino-4,5,6,7-tetrahydro-1,3-benzothiazole-2-amine; and
- a fixed-dose combinations comprising a pharmaceutical composition in dosage unit form comprising a NK1-antagonist Component (a) and 6-propylamino-4,5,6,7-tetrahydro-1,3-benzothiazole-2-amine Component (b), in admixture with a pharmaceutical carrier or vehicle, and its use for the treatment of a synucleinopathy in a patient.

The NK1-Antagonist Component (a).

As set forth above, any NK1-antagonist known for its use as an antiemetic agent is potentially useful for its combination with 6-propylamino-4,5,6,7-tetrahydro-1,3-benzothiazole-2-amine for the treatment of a synucleinopathy.

The long-term use of this combination slows the progression of a synucleinopathic disorder by mitigating or even eliminating the adverse effects induced by pramipexole, as such or as (S)-enantiomer in the racemate or in a (R)/(S)-mixture, and thereby enabling the use of high doses and thus more neuroprotective doses of pramipexole.

Advantageously, said NK1-antagonist is selected from the group consisting of
- 5-[[(2R,3S)-2-[(1R)-1-[3,5-bis(trifluoromethyl)phenyl]ethoxy]-3-(4-fluorophenyl)-4-morpholinyl]methyl]-1,2-dihydro-3H-1,2,4-triazol-3-one (aprepitant); described in U.S. Pat. No. 5,719,147, in a liquid oral formulation, in US 2017/0035774, and in an injectable emulsion in a single-dose vial for intravenous use containing 130 mg aprepitant in 18 ml of emulsion (Cinvanti®), described in U.S. Pat. No. 9,808,465 (the contents of each of which are incorporated herein in their entirety by reference);
- [3-{[(2R,3S)-2-[(1R)-1-[3,5-bis(trifluoromethyl)phenyl]ethoxy]-3-(4-fluorophenyl)morpholin-4-yl]methyl}-5-oxo-2H-1,2,4-triazol-1-yl]phosphonic acid (fosaprepitant), disclosed, for example as meglumine salt in U.S. Pat. No. 5,691,336 and as di(cyclohexylamine) salt in US 2016/0355533, the contents of each of which are incorporated herein in their entirety by reference;
- (2S,4S)-4-(4-Acetyl-1-piperazinyl)-N-[(1R)-1-[3,5-bis(trifluoromethyl)phenyl]ethyl]-2-(4-fluoro-2-methylphenyl)-N-methyl-1-piperidinecarboxamide (casopitant) described in U.S. Pat. No. 7,294,630, the contents of which are incorporated herein in its entirety by reference;
- (2S)-1-[(3aS,4S,7aS)-4-hydroxy-4-(2-methoxyphenyl)-7,7-diphenyl-1,3,3a,5,6,7a-hexahydroisoindol-2-yl]-2-(2-methoxyphenyl)propan-1-one (INN: dapitant)
- (2S,3S)—N-(5-tert-Butyl-2-methoxybenzyl)-2-(diphenylmethyl)-1-azabicyclo[2.2.2]octan-3-amine (maropitant), disclosed in U.S. Pat. No. 5,807,867, WO2005/082416 and EP 3173071 the contents of each of which are incorporated herein in their entirety by reference;
- (2S,3S)-2-Diphenylmethyl-3-[(5-isopropyl-2-methoxybenzyl)amino]quinuclidine (INN: ezlopitant), disclosed by Evangelista S (2001). "Ezlopitant. Pfizer"; Current Opinion in Investigational Drugs: 2 (10): 1441-3; reviewed in Drugs: the Investigational Drugs Journal 6 (8): 758-72, the contents of each of which are incorporated herein in their entirety by reference;
- (2S)—N-{2-[3,5-bis(trifluoromethyl)phenyl]ethyl}-2-[4-(cyclopropylmethyl)piperazin-1-yl]-N-methyl-2-phenylacetamide (INN: figopitant)
- N-[(2R)-1-[Acetyl-[(2-methoxyphenyl)methyl]amino]-3-(1H-indol-3-yl)propan-2-yl]-2-(4-piperidin-1-ylpiperidin-1-yl)acetamide (INN: lanepitant);
- 2-[3,5-bis(trifluoromethyl)phenyl]-N,2-dimethyl-N-[4-(2-methylphenyl)-6-(4-methyl-1-piperazinyl)-3-pyridinyl]propanamide (netupitant), described in U.S. Pat. Nos. 6,297,375, 6,593,472, 6,719,996, and, in an oral composition, comprising 300 mg of netupitant and palonosetron hydrochloride in an amount equivalent to 0.5 mg of palonosetron base, herein below referred to as "netupitant-300/palonosetron-0.5", in U.S. Pat. No. 8,951,969, the contents of each of which are incorporated herein in their entirety by reference;
- (2R,4S)-4-[(8aS)-6-oxo-1,3,4,7,8,8a-hexahydropyrrolo[1,2-a]pyrazin-2-yl]-N-[(1R)-1-[3,5-bis(trifluoromethyl)phenyl]ethyl]-2-(4-fluoro-2-methylphenyl)-N-methylpiperidine-1-carboxamide (INN: orvepitant), disclosed in US 2005/0176715 and, as crystalline maleate, in US 2011/0166150, the contents of each of which are incorporated herein in their entirety by reference;
- (5S,8S)-8-({(1R)-1-[3,5-bis(trifluoromethyl)phenyl]ethoxy}methyl)-8-phenyl-1,7-diazaspiro[4.5]decan-2-one (rolapitant), described in U.S. Pat. No. 7,049,320 and, for an injectable form thereof, in U.S. Pat. No. 9,101,615, the contents of each of which are incorporated herein in their entirety by reference;
- 3-((3aR,4R,5S,7aS)-5-[(1R)-1-[3,5-bis(trifluoromethylphenyl]ethoxy]-4-(4-fluorophenyl)-1,3,3a,4,5,6,7,7a-octahydroisoindol-2-ylcyclopent-2-en-1-one (serlopitant) described in U.S. Pat. Nos. 7,544,815 and 7,217,731, the contents of each of which are incorporated herein in their entirety by reference;
- 2-(S)-(4-Fluoro-2-methyl-phenyl)-piperazine-1-carboxylic acid [1-(R)-(3,5-bis-trifluoromethyl-phenyl)-ethyl]-methyl-amide (INN: vestipitant), described in WO 2001/25219 and, in intravenous formulation having a reduced tendency to cause hemolysis, in WO 2012/175434, the contents of each of which are incorporated herein in their entirety by reference; and (2S,3S)—N-[(2-methoxy-5-[5-(trifluoromethyl)tetrazol-1-yl]phenylmethyl]-2-phenylpiperidin-3-amine (INN: vofopitant), disclosed by Gardner C J et al. Regul Pept. 1996 Aug. 27; 65(1):45-53, the contents of which are incorporated herein in their entirety by reference.

Illustrative examples of pharmaceutically acceptable salts of basic advantageous NK1-antagonists include acid addition salts with mineral acids, such as hydrochloric acid, hydrobromic acid, hydriodic acid, sulfuric acid, phosphoric acid, nitric acid, carbonic acid, phosphoric acid and the like and acid addition salts with organic acids such as formic acid, acetic acid, propionic acid, oxalic acid, malonic acid, succinic acid, fumaric acid, maleic acid, lactic acid, malic acid, tartaric acid, citric acid, ascorbic acid, methanesulfonic acid, ethanesulfonic acid, gluconic acid, aspartic acid, glutamic acid. and the like.

Illustrative examples of pharmaceutically acceptable salts of acidic NK1-antagonists such as fosaprepitant include salts with inorganic bases such as alkaline metal or alkaline-earth metal salts, and salts with organic bases such as dicyclohexylamine salts, N-methyl-D-glucamine (meglumine) salts, and salts with amino acids, as described in U.S. Pat. No. 5,691,336, the contents of which are incorporated herein in their entirety by reference.

An advantageous NK1-antagonists to be used in combination with 6-propylamino-4,5,6,7-tetrahydro-1,3-benzothiazole-2-amine is selected from the group consisting of
  aprepitant and pharmaceutically acceptable salts and solvates thereof,
  fosaprepitant and pharmaceutically acceptable salts and solvates thereof,
  casopitant and pharmaceutically acceptable salts and solvates thereof,
  maropitant and pharmaceutically acceptable salts and solvates thereof,
  eziopitant and pharmaceutically acceptable salts and solvates thereof,
  lanepitant and pharmaceutically acceptable salts and solvates thereof,
  netupitant and pharmaceutically acceptable salts and solvates thereof,
  orvapitant and pharmaceutically acceptable salts and solvates thereof,
  rolapitant and pharmaceutically acceptable salts and solvates thereof,
  serlopitant and pharmaceutically acceptable salts and solvates thereof,
  vestipitant and pharmaceutically acceptable salts and solvates thereof,
  vofopitant and pharmaceutically acceptable salts and solvates thereof, and
  netupitant-300/palonosetron-0.5.

Aprepitant, fosaprepitant meglumine, fosaprepitant di(cyclohexylamine), rolapitant, rolapitant hydrochloride and netupitant-300/palonosetron-0.5 are particularly advantageous NK1-antagonists.

Antagonists of the NK1 receptor that are approved for the prevention or treatment of postoperative nausea and vomiting or for the prevention of chemotherapy-induced nausea and vomiting are particularly useful according to the present invention. Aprepitant, commercially available (Emend®) in capsules containing 40 mg, 80 mg, or 125 mg aprepitant; fosaprepitant meglumine, commercially available (Emend® Injection), in vials containing 115 mg or 150 mg fosaprepitant; rolapitant, available (Varubi®) in 90-mg tablets; and netupitant-300/palonostron-0.5, available (Akynzeo®) in a fixed-dose combination in capsules containing 300 mg of netupitant and 0.5 mg of the NK1-antagonist palonosetron (as hydrochloride); are preferred NK1-antagonists.

In the aforementioned method, use and combination, including fixed-dose combinations, said NK1-antagonist is present in an amount per unit form and is administered at a daily dose of 1 µg to 600 mg, normally from 1 mg to 600 mg, or from 1 mg to 300 mg.

More particularly, in said combination, said NK1-antagonist is selected from the group consisting of aprepitant and pharmaceutically acceptable salts and solvates thereof, at a daily dose equivalent to from 10 mg to 250 mg of aprepitant; fosaprepitant and pharmaceutically acceptable salts and solvates thereof, at a daily dose equivalent to from 10 mg to 250 mg of aprepitant; rolapitant and pharmaceutically acceptable salts and solvates thereof, at a daily dose equivalent to from 15 mg to 270 mg of rolapitant, netupitant and pharmaceutically acceptable salts and solvates thereof, at a daily dose equivalent to from 300 mg to 600 mg; and netupitant-300/palonosetron-0.5.

For its administration to a patient suffering from a synucleinopathy in combination with 6-propylamino-4,5,6,7-tetrahydro-1,3-benzothiazole-2-amine, each of the above NK1-antagonists is formulated in a pharmaceutical composition in dosage unit form comprising, as an active ingredient, said NK1-antagonist, in admixture with a pharmaceutical carrier or vehicle.

In particular, said NK1-antagonist active ingredient of said pharmaceutical composition is selected from the group consisting of aprepitant and pharmaceutically acceptable salts and solvates thereof, in an amount, per unit form, equivalent to from 10 mg to 250 mg of aprepitant; fosaprepitant and pharmaceutically acceptable salts and solvates thereof, in an amount, per unit form, equivalent to from 10 mg to 250 mg of aprepitant; rolapitant and pharmaceutically acceptable salts and solvates thereof, in an amount, per unit form, equivalent to from 15 mg to 270 mg of rolapitant; netupitant and pharmaceutically acceptable salts and solvates thereof, in an amount, per unit form, equivalent to from 300 mg to 600 mg; and netupitant-300/palonosetron-0.5.

Advantageously, said NK1-antagonist is aprepitant, in an amount per unit form of from 10 mg to 250 mg; fosaprepitant meglumine, in an amount per unit form equivalent to from 10 mg to 250 mg of aprepitant; or rolapitant, in an amount per unit form of from 15 mg to 270 mg or from 30 mg to 270 mg.

As set forth above, by using a NK1-antagonist in combination with pramipexole or a pharmaceutically acceptable salt or solvate thereof, it is possible to treat a patient suffering from a synucleinopathy by maintaining a therapeutically effective pramipexole or pharmaceutically acceptable salt or solvate thereof daily dose with minimal adverse effect.

Thus, in order to assure a sure, safe and concurrent administration of said NK1-antagonist and said 6-propylamino-4,5,6,7-tetrahydro-1,3-benzothiazole-2-amine, the present invention provides a fixed-dose combination consisting of a pharmaceutical composition in dosage unit form comprising an effective amount per unit form of said NK1-antagonist and an effective amount per unit form of said 6-propylamino-4,5,6,7-tetrahydro-1,3-benzothiazole-2-amine, in admixture with a pharmaceutical carrier or vehicle.

These NK1-antagonist/6-propylamino-4,5,6,7-tetrahydro-1,3-benzothiazole-2-amine fixed-dose combinations are illustrated in "The Pharmaceutical Compositions" section below.

The 6-propylamino-4,5,6,7-tetrahydro-1,3-benzothiazole-2-amine Component (b).

As set forth in the above definitions, the 6-propylamino-4,5,6,7-tetrahydro-1,3-benzothiazole-2-amine is selected from the group consisting of
- pramipexole, i.e. (S)-6-propylamino-4,5,6,7-tetrahydro-1,3-benzothiazole-2-amine, and pharmaceutically acceptable salts and solvates thereof;
- the racemate, i.e. (R,S)-6-propylamino-4,5,6,7-tetrahydro-1,3-benzothiazole-2-amine, and pharmaceutically acceptable salts and solvates thereof; and
- a (S)/(R)-mixture, i.e. a mixture of (R)-6-propylamino-4,5,6,7-tetrahydro-1,3-benzothiazole-2-amine and (S)-6-propylamino-4,5,6,7-tetrahydro-1,3-benzothiazole-2-amine, normally in a pharmaceutical composition, for example as described in US 2008/0014259, (the contents of which are incorporated herein in their entirety by reference) containing a therapeutically effective amount of (S)-enantiomer, in admixture with a pharmaceutical carrier or vehicle.

Illustrative examples of pharmaceutically acceptable salts or solvates of 6-propylamino-4,5,6,7-tetrahydro-1,3-benzothiazole-2-amine are derived from inorganic or organic acids such as hydrochloric acid, hydrobromic acid, sulfuric acid, sulfamic acid, phosphoric acid, nitric acid, acetic acid, propionic acid, stearic acid, glycolic acid, oxalic acid, succinic acid, lactic acid, maleic acid, hydroxymaleic acid, fumaric acid, malic acid, tartaric acid, citric acid, ascorbic acid, phenylacetic acid, glutamic acid, benzoic acid, salicylic acid, 2-acetoxybenzoic acid, methanesulfonic acid, ethanesulfonic acid, 2-hydroxyethanesulfonic (isethionic) acid, p-toluenesulfonic acid, 2-naphthalenesulfonic acid, 4-amino-benzenesulfonic (sulfanilic) acid, 2,6-naphthalenedisulfonic acid, 1,5-naphthalenedisulfonic acid, and pamoic (embonic) acid. The solvation solvent is normally water.

In the case of pramipexole or pharmaceutically acceptable salt or solvate thereof, pramipexole dihydrochloride monohydrate, commercially available, is the preferred 6-propylamino-4,5,6,7-tetrahydro-1,3-benzothiazole-2-amine. For example, stable pharmaceutical compositions comprising pramipexole dihydrochloride monohydrate, disclosed in WO 2012/0140604 and in WO 2008/122638, the contents of each of which are incorporated herein by reference in their entirety; and sustained release compositions comprising pramipexole dihydrochloride monohydrate, disclosed in U.S. Pat. No. 8,399,016, incorporated herein by reference in its entirety, may be useful for use in combination with a NK1-antagonist for the treatment of a synucleinopathy.

The racemate and pramipexole, described in U.S. Pat. No. 4,886,812 the contents of which are incorporated herein in their entirety by reference, are each a useful 6-propylamino-4,5,6,7-tetrahydro-1,3-benzothiazole-2-amine for the treatment of a synucleinopathy in combination with a NK1-antagonist.

A (S)/(R)-mixture, i.e. a pharmaceutical composition comprising a therapeutically effective amount of (R)-6-propylamino-4,5,6,7-tetrahydro-1,3-benzothiazole-2-amine or pharmaceutically acceptable salts and solvates thereof and a therapeutically effective amount of (S)-6-propylamino-4,5,6,7-tetrahydro-1,3-benzothiazole-2-amine or pharmaceutically acceptable salts and solvates thereof, as disclosed in US 2008/0014259, also is a 6-propylamino-4,5,6,7-tetrahydro-1,3-benzothiazole-2-amine useful for the treatment of a synucleinopathy in combination with a NK1-antagonist.

For the treatment of synucleinopathies, in combination with a NK1-antagonist as illustrated in "The NK1-antagonist Component (a)" section above, the 6-propylamino-4,5,6,7-tetrahydro-1,3-benzothiazole-2-amine is formulated in a pharmaceutical composition comprising said 6-propylamino-4,5,6,7-tetrahydro-1,3-benzothiazole-2-amine in an amount equivalent to from 0.125 mg to 3000 mg of pramipexole dihydrochloride monohydrate in admixture with a pharmaceutical carrier or vehicle. Said composition is administered to a patient in need of said treatment at daily dose of from 0.375 mg to 3000 mg in combination with a NK1-antagonist at a daily dose of 1 µg to 600 mg, normally from 1 mg to 600 mg.

According to the present invention, the 6-propylamino-4,5,6,7-tetrahydro-1,3-benzothiazole-2-amine is preferably selected from the group consisting of
- (S)-6-propylamino-4,5,6,7-tetrahydro-1,3-benzothiazole-2-amine (INN: pramipexole) and pharmaceutically acceptable salts and solvates thereof, in particular its dihydrochloride monohydrate (USAN: pramipexole hydrochloride), in a dose per unit form equivalent to from 0.125 mg to 45 mg, preferably from 0.125 mg to 40-42 mg of pramipexole dihydrochloride monohydrate;
- (R,S)-6-propylamino-4,5,6,7-tetrahydro-1,3-benzothiazole-2-amine (the racemate) and pharmaceutically acceptable salts an solvates thereof, in a dose per unit form equivalent to from 0.25 mg to 90 mg of pramipexole dihydrochloride monohydrate (thus, obviously, including a dose per unit form of (S)-6-propylamino-4,5,6,7-tetrahydro-1,3-benzothiazole-2-amine equivalent to from 0.125 mg to 45 mg, preferably from 0.125 mg to 40-42 mg of pramipexole dihydrochloride monohydrate, and a dose per unit form of (R)-6-propylamino-4,5,6,7-tetrahydro-1,3-benzothiazole-2-amine equivalent to from 0.125 mg to 45 mg, preferably from 0.125 mg to 40 mg of pramipexole dihydrochloride monohydrate), and preferably, from 0.25 mg to 90 mg, preferably from 0.25 mg to 80-84 mg of pramipexole dihydrochloride monohydrate (thus, obviously, including a dose per unit form of (S)-6-propylamino-4,5,6,7-tetrahydro-1,3-benzothiazole-2-amine equivalent to from 0.125 mg to 40-42 mg of pramipexole dihydrochloride monohydrate, and a dose per unit form of (R)-6-propylamino-4,5,6,7-tetrahydro-1,3-benzothiazole-2-amine equivalent to from 0.125 mg to 40-42 mg of pramipexole dihydrochloride monohydrate); and
- a (R)/(S)-mixture, i.e. a pharmaceutical composition in dosage unit form comprising 6-propylamino-4,5,6,7-tetrahydro-1,3-benzothiazole-2-amine, at a dose per unit form equivalent to from 50 mg to 3000 mg, preferably to from 150 mg to 3000 mg, of pramipexole dihydrochloride monohydrate, said amount per unit form including a (S)-enantiomer amount equivalent to from 0.125 mg to 45 mg, preferably from 0.125 mg to 45 mg of pramipexole dihydrate monohydrate (thus, obviously, said amount per unit form being constituted by an amount of (S)-enantiomer equivalent to from 0.125 mg to 45 mg, preferably from 0.125 mg to 40-42 mg of pramipexole dihydrochloride monohydrate and by a (R)-6-propylamino-4,5,6,7-tetrahydro-1,3-benzothiazole-2-amine amount per unit form equivalent to from 50 mg, preferably from 150 mg, to 3000 mg (minus from 0.125 mg to 45 mg, normally from 0.125 to 40-42 mg) of pramipexole dihydrochloride monohydrate), and preferably, from 0.125 mg to 40-42 mg of pramipexole dihydrochloride monohydrate (thus, obviously, said amount per unit form being constituted by an amount of (S)-enantiomer equivalent to from 0.125 mg to 45 mg, preferably from 0.125 mg to 40-42 mg of pramipexole dihydrochloride monohydrate and by a (R)-6-propylamino-4,5,6,7-tetrahydro-1,3-benzothiazole-2-amine amount per unit form equivalent to from 50 mg, preferably from 150 mg, to 3000 mg (minus from 0.125 mg to 45 mg, preferably from 0.125 to 40-42 mg) of pramipexole dihydrochloride monohydrate).

As set forth in the definitions, the effective daily dose of pramipexole or of (S)-enantiomer is a dose equivalent to at least the pramipexole dihydrochloride monohydrate approved daily dose for the treatment of PD. Said daily approved dose is from 0.375 mg to 4.5 mg. However, it is hereby specified that, according to the present invention, the combination of a NK1-antagonist with said pramipexole or (S)-enantiomer allows the administration of pramipexole dihydrochloride monohydrate approved daily doses for the treatment of Parkinson's disease without any adverse effect, but also allows the administration of pramipexole dihydrochloride monohydrate daily doses that are higher and also much higher than said approved doses.

In particular, in said combination with a NK1-antagonist, pramipexole dihydrochloride monohydrate may be administered to a patient, including pediatric patients, suffering from a synucleinopathy at a daily dose of from 0.375 mg to 45 mg, preferably from 0.375 mg to 40-42 mg, depending on the tolerability (in combination with the NK1-antagonist). According to the present invention, the daily dose range of from 0.375 mg to 45 mg, preferably from 0.375 mg to 40-42 mg includes low doses to be administered during a titration period. More particularly, said daily dose range may be selected from the group consisting of form 1.5 mg to 45 mg, from 1.6 mg to 45 mg, from 1.625 mg to 45 mg, from 3 mg to 45 mg, from more than 4.5 mg to 45 mg, from 4.8 to 45 mg, from more than 6 mg to 45 mg, and from 6.5 mg to 45 mg. Preferably, said daily dose range may be selected from the group consisting of from 1.5 mg to 40-42 mg, from 1.6 mg to 40-42 mg, from 1.625 mg to 40-42 mg, from 3 mg to 40-42 mg, from more than 4.5 mg to 40-42 mg, from 4.8 mg to 40-42 mg, from more than 6 mg to 40-42 mg, from more than 10 mg to 40-42 mg, from 13.5 mg to 40-42 mg, from 13.5 mg to 30 mg, and from 13.5 mg to 20-21 mg depending on the tolerability (in combination with the NK1-antagonist).

For its administration to a patient suffering from a synucleinopathy in combination with an NK1-antagonist as illustrated above in "The NK1-Antagonist Component (a)" section, the 6-propylamino-4,5,6,7-tetrahydro-1,3-benzothiazole-2-amine is formulated in a pharmaceutical composition in dosage unit form comprising, as an active ingredient, said 6-propylamino-4,5,6,7-tetrahydro-1,3-benzothiazole-2-amine, in admixture with a pharmaceutical carrier or vehicle.

According to the present invention, said pharmaceutical composition Component (b) comprises, as an active ingredient, pramipexole or a pharmaceutically acceptable salt thereof in an amount per unit form equivalent to from 0.125 mg to 30 mg or 20-21 mg, normally from 1.5 mg to 10 mg of pramipexole dihydrochloride monohydrate, in an IR-formulation, or in an amount per unit form equivalent to from 1.5 to 45 mg, preferably from 1.5 mg to 40-42 mg of pramipexole dihydrochloride monohydrate in an ER-formulation.

More particularly, said pramipexole is present in said composition in an amount-range per unit form equivalent to a pramipexole dihydrochloride monohydrate amount-range per unit form selected from the group consisting of from 0.125 to 45 mg, preferably from 1.5 mg to 45 mg, from 1.625 mg to 45 mg, from 3 mg to 45 mg, from more than 4.5 mg to 45 mg, from 4.8 mg to 45 mg, from more than 6 mg to 45 mg, and from more than 10 mg to 45 mg. Especially said pramipexole is present in said composition in an amount-range per unit form equivalent to a pramipexole dihydrochloride monohydrate amount-range per unit form selected from the group consisting of from 0.125 mg to 40-42 mg, from 0.125 mg to 30 mg, from 0.125 to 20-21 mg, from 1.5 mg to 40-42 mg, from 1.625 mg to 40-42 mg, from 3 mg to 40-42 mg, from more than 4.5 mg to 40-42 mg, from 4.8 mg to 40-42 mg, from more than 6 mg to 40-42 mg, and from more than 10 mg to 40-42 mg.

In a preferred embodiment, the invention provides a pharmaceutical composition in dosage unit form comprising, as an active ingredient, pramipexole and pharmaceutically acceptable salts and solvates thereof, in an amount per unit form equivalent to from 13.5 mg to 45 mg, from 13.5 mg to 40-42 mg, from 13.5 mg to 30 mg or from 13.5 mg to 20-21 mg of pramipexole dihydrochloride monohydrate, in admixture with a pharmaceutical carrier or vehicle.

As set forth above, a NK1-antagonist, in combination with pramipexole or a pharmaceutically acceptable salt or solvate thereof, it is possible to treat a patient suffering from a synucleinopathy by maintaining a therapeutically effective pramipexole or pharmaceutically acceptable salt or solvate thereof daily dose with minimal adverse effect.

In order to provide concurrent administration of said NK1-antagonist and of said pramipexole or a pharmaceutically acceptable salt or solvate thereof, the invention provides a fixed-dose combination consisting of a pharmaceutical composition in dosage unit form comprising, as active ingredients, a NK1-antagonist; and pramipexole and pharmaceutically acceptable salts and solvates thereof, in admixture with a pharmaceutical carrier or vehicle.

The NK1-antagonist/-6-propylamino-4,5,6,7-tetrahydro-1,3-benzothiazole-2-amine fixed-dose combinations will be illustrated in "The Pharmaceutical Compositions" section below.

Specific Aspects of the Invention

According to a first aspect, the present invention includes a method for safely slowing or even reversing disease progression of patients suffering from a synucleinopathy and treated with 6-propylamino-4,5,6,7-tetrahydro-1,3-benzothiazole-2-amine, by concurrently and chronically administering to said patients a NK1-antagonist.

More particularly, the invention provides a method for treating a synucleinopathy in a patient, which comprises administering to said patient in need of said treatment an effective daily dose of a NK1-antagonist in combination with an effective daily dose of 6-propylamino-4,5,6,7-tetrahydro-1,3-benzothiazole-2-amine.

Any of the NK1-antagonists described in "The NK1-antagonist Component (a)" section may be used according to the method of this aspect of the invention.

In carrying out the method of the present invention, the daily dose of these NK1-antagonists is at least as high as that for preventing or treating nausea and vomiting in patients undergoing a surgical operation or cancer chemotherapy according to the current protocols for said treatment or prevention. Said daily dose is from 1 µg to 600 mg, normally from 1 mg to 600 mg, or from 1 mg to 300 mg.

A NK1-antagonist selected from the group consisting of aprepitant and pharmaceutically acceptable salts and solvates thereof and rolapitant and pharmaceutically acceptable salt and solvate thereof is a particularly advantageous NK1-antagonist.

As set forth above, the 6-propylamino-4,5,6,7-tetrahydro-1,3-benzothiazole-2-amine is selected from the group consisting of the racemate, pramipexole, and (R)/(S)-mixtures and pharmaceutically acceptable salts and solvates thereof.

The doses per unit form and the daily doses of the 6-propylamino-4,5,6,7-tetrahydro-1,3-benzothiazole-2-amine are illustrated above in "The 6-propylamino-4,5,6,7-tetrahydro-1,3-benzothiazole-2-amine" section. Said 6-propylamino-4,5,6,7-tetrahydro-1,3-benzothiazole-2-amine dose per unit form consists of or includes an (S)-isomer amount per unit form equivalent to from 0.125 mg to 45 mg, preferably from more than 6 mg to 45 mg, normally from 0.125 mg to 40-42 mg, preferably from more than 6 mg to 40-42 mg of pramipexole dihydrochloride monohydrate.

According to an embodiment, the 6-propylamino-4,5,6,7-tetrahydro-1,3-benzothiazole-2-amine is selected from the group consisting of
- (S)-6-propylamino-4,5,6,7-tetrahydro-1,3-benzothiazole-2-amine (INN: pramipexole) and pharmaceutically acceptable salts thereof, in particular its dihydrochloride monohydrate (USAN: pramipexole hydrochloride), in a dose/unit form equivalent to from 0.125 mg to 45 mg, preferably from 0.125 mg to 40-42 mg of pramipexole dihydrochloride monohydrate, to be administered in a daily dose equivalent to from 0.375 mg to 45 mg, preferably from more than 6 mg to 45 mg or from 6.5 mg to 45 mg, normally from 0.375 mg to 40-42 mg, preferably from more than 6 mg to 40-42 mg or from 6.5 mg to 40-42 mg of pramipexole dihydrochloride monohydrate;
- (R,S)-6-propylamino-4,5,6,7-tetrahydro-1,3-benzothiazole-2-amine (the racemate) and pharmaceutically acceptable salts thereof, in a dose/unit form of from 0.25 mg to 90 mg, preferably from more than 12 mg to 90 mg, normally from 0.25 mg to 80 mg, said dose being inclusive of an S-enantiomer amount per unit form equivalent to from 0.125 mg to 45 mg, preferably from more than 12 mg to 45 mg or from 13 mg to 45 mg, normally from 0.125 mg to 40-42 mg, preferably from more than 12 mg to 40-42 mg or from 13 mg to 40-42 mg, of pramipexole dihydrochloride monohydrate, administered in a daily dose equivalent to from 0.375 mg to 45 mg, preferably from more than 12 mg to 45 mg or from 13 mg to 45 mg, normally from 0.375 mg to 40-42 mg, preferably from more than 12 mg to 40-42 mg or from 13 mg to 40-42 mg, of pramipexole dihydrochloride monohydrate; and
- a (S)/(R)-mixture that is a pharmaceutical composition in dosage unit form comprising 6-propylamino-4,5,6,7-tetrahydro-1,3-benzothiazole-2-amine, in a dose per unit form of from 50 mg to 3000 mg, preferably from 150 mg to 3000 mg, said dose being inclusive of a S-enantiomer amount per unit form equivalent to from 0.125 to 45 mg, preferably from more than 6 mg to 45 mg or from 6.5 mg to 45 mg, normally from 0.125 to 40-42 mg, preferably from more than 6 mg to 40-42 mg or from 6.5 mg to 40-42 mg, of pramipexole dihydrochloride monohydrate, administered at a daily dose of from 150 mg to 300 mg, preferably from 300 mg to 3000 mg or from 450 mg to 3000 mg, inclusive of a (S)-enantiomer daily dose equivalent to from 0.375 to 45 mg, preferably from more than 6 mg to 45 mg or from 6.5 mg to 45 mg, normally from 0.375 mg to 40-42 mg, preferably from more than 6 mg to 40-42 mg or from 6.5 mg to 40-42 mg, of pramipexole dihydrochloride monohydrate.

In the method for the treatment of a synucleinopathy according to the present invention, the NK1-antagonist, at the aforementioned effective daily dose, is normally administered to a patient in need of said treatment in combination with pramipexole dihydrochloride monohydrate. Said pramipexole dihydrochloride monohydrate, in a pharmaceutical composition in admixture with a pharmaceutical carrier or vehicle, is administered to said patient at a daily dose of 0.375 mg to 45 mg, preferably from 0.375 mg to 40-42 mg.

According to an embodiment,
said NK1-antagonist is selected from the group consisting of aprepitant and pharmaceutically acceptable salts and solvates thereof, fosaprepitant and pharmaceutically acceptable salts and solvates thereof, rolapitant and pharmaceutically acceptable salts and solvates thereof, netupitant and pharmaceutically acceptable salts and solvates thereof, each at a daily dose illustrated in "The NK1-antagonist" section, and netupitant-300/palonosetron-0.5 once a day or every 2-4 days; and said 6-propylamino-4,5,6,7-tetrahydro-1,3-benzothiazole-2-amine is selected from the group consisting of pramipexole and pharmaceutically acceptable salts and solvates thereof, at a daily dose as illustrated above in "The 6-propylamino-4,5,6,7-tetrahydro-1,3-benzothiazole-2-amine Component (b)" section.

According to an advantageous embodiment, in the method of the present invention the NK1-antagonist is aprepitant, fosaprepitant meglumine, or rolapitant and the 6-propylamino-4,5,6,7-tetrahydro-1,3-benzothiazole-2-amine or a pharmaceutically acceptable salt or solvate thereof is pramipexole dihydrochloride monohydrate, each at the daily doses illustrated in the respective sections.

According to a particular embodiment, in said method (or use), said NK1-antagonist, at the aforementioned effective daily dose, is administered to said patient in combination with pramipexole dihydrochloride monohydrate, administered to said patient at a daily dose of from 1.5 mg to 45 mg, normally from 1.5 mg to 45 mg, preferably from 1.5 mg to 40-42 mg, normally from 1.5 mg to 20-21 mg.

Preferably, in the method for treating a synucleinopathy in a patient according to the present invention,
said NK1-antagonist is aprepitant, at a daily oral dose of from 10 mg to 250 mg; fosaprepitant meglumine, at daily injectable dose equivalent to from 10 mg to 250 mg of aprepitant; or rolapitant, at a daily oral dose of from 15 mg to 270 mg from 30 mg to 270 mg; or netupitant-300/palonosetron-0.5; and said 6-propylamino-4,5,6,7-tetrahydro-1,3-benzothiazole-2-amine or a pharmaceutically acceptable salt or solvate thereof is pramipexole dihydrochloride monohydrate, at an effective daily oral dose of from 1.5 mg to 45 mg, normally from 1.5 mg to 22.5 mg, preferably from 1.5 mg to 40-42 mg, normally from 1.5 mg to 20-21 mg.

Said NK1-antagonist and said 6-propylamino-4,5,6,7-tetrahydro-1,3-benzothiazole-2-amine may also be co-formulated in a pharmaceutical composition, in admixture with a pharmaceutical carrier or vehicle as illustrate herein below.

The method of the present invention allows a safe treatment of synucleinopathies such as Parkinson's disease, Lewy body dementia, mutations in the glucocerebrosidase gene, multiple system atrophy Alzheimer's disease, the Lewy body variant of Alzheimer's disease, neurodegeneration with brain iron accumulation, and parkinsonian disorders associated with glucocerebrosidase (GBA) mutations.

According to a second aspect, the invention provides a NK1-antagonist for use in combination with 6-propylamino-4,5,6,7-tetrahydro-1,3-benzothiazole-2-amine, in the treatment of a synucleinopathy in a patient in need of said treatment.

Any of the NK1-antagonists illustrated in "The NK1-antagonist Component (a)" section may be used, normally in a dosage unit form, according to this second aspect of the invention.

In particular, this second aspect of the present invention provides a NK1-antagonist, in an amount per unit form of from 1 µg to 600 mg, normally from 1 mg to 600 mg or from 1 mg to 300 mg, for use in combination with a daily dose of said 6-propylamino-4,5,6,7-tetrahydro-1,3-benzothiazole-2-amine of from 0.375 mg to 3000 mg, for the treatment of a synucleinopathy in a patient in need of said treatment.

For the use according to of the present invention, the daily dose of these NK1-antagonists is at least as high as that for preventing or treating nausea and vomiting in patients undergoing a surgical operation or cancer chemotherapy according to the current protocols for said treatment or prevention. Said daily dose will range from 1 µg to 600 mg, normally from 1 mg to 600 mg or from 1 mg to 300 mg.

For its use for the treatment of a synucleinopathy according to the present invention, the NK1-antagonist, at the aforementioned effective daily dose, as illustrated in "The NK1-antagonist Component (a)" section, is administered to a patient in need of said treatment in combination with 6-propylamino-4,5,6,7-tetrahydro-1,3-benzothiazole-2-amine at the aforementioned effective daily dose, as illustrated in "The 6-propylamino-4,5,6,7-tetrahydro-1,3-benzothiazole-2-amine Component (b)" section.

According to an embodiment said NK1-antagonist, normally in an amount per unit form of from 1 µg to 600 mg, normally from 1 mg to 600 mg or from 1 mg to 300 mg, is for use in combination with 6-propylamino-4,5,6,7-tetrahydro-1,3-benzothiazole-2-amine, as a (R)/(S)-mixture, at a daily dose of from 50 to 3000 mg, from 150 mg to 3000 mg or from 300 mg to 3000 mg, said daily dose including a (S)-enantiomer dose equivalent to from 0.375 mg to 45 mg, preferably to from more than 6 mg to 45 mg or from 6.5 mg to 45 mg, normally from 0.375 mg to 40-42 mg, preferably to from more than 6 mg to 40-42 mg or from 6.5 mg to 40-42 mg, of pramipexole dihydrochloride monohydrate.

Said 6-propylamino-4,5,6,7-tetrahydro-1,3-benzothiazole-2-amine may also be a racemate, at a daily dose equivalent to from 0.75 mg to 90 mg, preferably to from more than 12 mg to 90 mg or from 13 mg to 90 mg, normally from 0.75 mg to 80 mg, preferably to from more than 12 mg to 80 mg or from 13 mg to 80 mg, of pramipexole dihydrochloride monohydrate, thus delivering a (S)-enantiomer daily dose equivalent to from 0.75 mg to 40-42 mg, preferably to from more than 12 mg to 40-42 mg or from 13 mg to 40-42 mg, from 0.75 mg to 40-42 mg, preferably to from more than 12 mg to 40-42 mg or from 13 mg to 40-42 mg, of pramipexole dihydrochloride monohydrate.

Preferably, said 6-propylamino-4,5,6,7-tetrahydro-1,3-benzothiazole-2-amine is pramipexole or pharmaceutically acceptable salt or solvate thereof, at a daily dose equivalent to from 1.5 mg to 45 mg, advantageously from more than 4.5 mg to 45 mg, more advantageously from 4.8 mg to 45 mg, preferably from more than 6 mg to 45 mg or from 6.5 mg to 45 mg, normally from 1.5 mg to 40-42 mg, advantageously from more than 4.5 mg to 40-42 mg, more advantageously from 4.8 mg to 40-42 mg, preferably from more than 6 mg to 40-42 mg or from 6.5 mg to 40-42 mg of pramipexole dihydrochloride monohydrate.

For the treatment of a synucleinopathy, the NK1-antagonist and the 6-propylamino-4,5,6,7-tetrahydro-1,3-benzothiazole-2-amine are each formulated in a pharmaceutical composition in dosage unit form comprising said NK1-antagonist and, respectively, said 6-propylamino-4,5,6,7-tetrahydro-1,3-benzothiazole-2-amine, each in admixture with a pharmaceutical carrier or vehicle.

In general, said NK1-antagonist and said 6-propylamino-4,5,6,7-tetrahydro-1,3-benzothiazole-2-amine are each formulated in a pharmaceutical composition in dosage unit form comprising said NK1-antagonist in an amount per unit form of from 1 µg to 600 mg; and, respectively, said 6-propylamino-4,5,6,7-tetrahydro-1,3-benzothiazole-2-amine in an amount per unit of from 0.125 mg to 3000 mg, each in admixture with a pharmaceutical carrier or vehicle.

In particular, according to this second aspect, the invention provides a pharmaceutical combination comprising Component (a): a NK1-antagonist, in a pharmaceutical composition in dosage unit form comprising, as an active ingredient, said NK1-antagonist in an amount per unit form of from 1 µg to 600 mg, normally from 1 mg to 600 mg or from 1 mg to 300 mg, in admixture with a pharmaceutical carrier or vehicle; and Component (b): a 6-propylamino-4,5,6,7-tetrahydro-1,3-benzothiazole-2-amine selected from the group consisting of pramipexole and pharmaceutically acceptable salts thereof, in a daily dose equivalent to from 0.375 mg to 45 mg, preferably from 0.375 mg to 40-42 mg of pramipexole dihydrochloride monohydrate, for use in the treatment of a synucleinopathy in a patient in need of said treatment.

Preferably, said 6-propylamino-4,5,6,7-tetrahydro-1,3-benzothiazole-2-amine is pramipexole dihydrochloride monohydrate, also in a pharmaceutical composition in dosage unit form in an amount per unit form of from more than 4.5 mg to 45 mg, from more than 6 mg to 45 mg or from 6.5 mg to 45 mg, preferably from more than 4.5 mg to 40-42 mg, from more than 6 mg to 40-42 mg or from 6.5 mg to 40-42 mg.

Advantageously, said NK1-antagonist Component (a) is selected from the group consisting of aprepitant and pharmaceutically acceptable salts and solvates thereof, fosaprepitant and pharmaceutically acceptable salts and solvates thereof, rolapitant and pharmaceutically acceptable salts and solvates thereof, netupitant and pharmaceutically acceptable salts and solvates thereof, each in an amount per unit form as illustrated in "The NK1-antagonist Component (a)" section, and netupitant-300/palonosetron-0.5.

Preferably, said NK1-antagonist is aprepitant, at a daily oral dose of from 10 mg to 250 mg; fosaprepitant meglumine, at an effective daily injectable dose equivalent to from 10 mg to 250 mg of aprepitant; rolapitant, at an effective daily oral dose of from 15 mg to 270 mg or from 30 mg to 270 mg; or netupitant-300/palonosetron-0.5.

The use according to the present invention is made under conditions illustrated herein above for carrying out the method of treatment.

According to this second aspect, the invention also provides a pharmaceutical combination comprising
(a) a NK1-antagonist; and
(b) a 6-propylamino-4,5,6,7-tetrahydro-1,3-benzothiazole-2-amine, useful for the treatment of a synucleinopathy.

For this purpose, any of the NK1-antagonists illustrated in "The NK1-antagonist Component (a)" section may be used according to the method of this aspect of the invention.

Normally, the NK1-antagonist Component (a) is used at a dose that is at least as high as the dose approved for the prevention or treatment of postoperative nausea and vomiting or for the prevention of the chemotherapy-induced nausea and vomiting; and the 6-propylamino-4,5,6,7-tetrahydro-1,3-benzothiazole-2-amine Component (b) is used according to the conventional protocols for the treatment of a synucleinopathy such as PD.

The amounts per unit form and the daily doses of the NK1-antagonist and of the 6-propylamino-4,5,6,7-tetrahydro-1,3-benzothiazole-2-amine are those illustrated in the description of the first and herein above in this second aspect of the present invention.

According to a third aspect, the invention provides the use of a NK1-antagonist for the preparation of a medicament for treating a synucleinopathy in a patient in need of said treatment, in combination with with an effective daily dose of 6-propylamino-4,5,6,7-tetrahydro-1,3-benzothiazole-2-amine.

For this use, said NK1-antagonist is formulated in a pharmaceutical composition comprising, as an active ingredient, said NK1-antagonist, in admixture with a pharmaceutical carrier or vehicle, to be administered, concurrently or sequentially, in combination with 6-propylamino-4,5,6,7-tetrahydro-1,3-benzothiazole-2-amine, for the treatment of a synucleinopathy in a patient in need of said treatment.

In said pharmaceutical composition, said NK1-antagonist is in admixture with a pharmaceutical carrier and formulated in unit forms for oral, intravenous, transcutaneous, and/or transdermal administration, as described below.

Any of the NK1-antagonists described in "The NK1-antagonist Component (a)" section may be used as an active ingredient of the pharmaceutical composition indicated as a medicament for the treatment of a synucleinopathy in combination with 6-propylamino-4,5,6,7-tetrahydro-1,3-benzothiazole-2-amine described in "The 6-propylamino-4,5,6,7-tetrahydro-1,3-benzothiazole-2-amine Component (b)" section according to this third aspect of the present invention.

According to an embodiment of this third aspect, said medicament is a pharmaceutical composition in dosage unit form comprising, as an active ingredient, said NK1-antagonist in an amount per unit form of from 1 μg to 600 mg, normally from 1 mg to 600 mg or from 1 mg to 300 mg, in admixture with a pharmaceutical carrier or vehicle. This medicament is destined to be administered to a patient suffering from a synucleinopathy, in combination with 6-propylamino-4,5,6,7-tetrahydro-1,3-benzothiazole-2-amine daily dose of from 0.375 mg to 3000 mg, inclusive of a (S)-enantiomer amount of from 0.375 mg to 45 mg, preferably from 0.375 mg to 40-42 mg.

These daily doses of 6-propylamino-4,5,6,7-tetrahydro-1, 3-benzothiazole-2-amine include low pramipexole daily doses useful for the administration during the titration period. At the end of said titration period, the medicament thus manufactured enables the safe intake of pramipexole daily doses never heretofore attained (without the combination with the NK1-antagonist) as shown in the Component (b) section.

In particular, said NK1-antagonist active ingredient is selected from the group consisting of aprepitant and pharmaceutically acceptable salts and solvates thereof, in an amount, per unit form, equivalent to from 10 mg to 250 of aprepitant; fosaprepitant and pharmaceutically acceptable salts and solvates thereof, in an amount, per unit form, equivalent to from 10 mg to 250 of aprepitant; rolapitant and pharmaceutically acceptable salts and solvates thereof, in an amount, per unit form, equivalent to from 15 mg to 270 mg of rolapitant; netupitant and pharmaceutically acceptable salts and solvates thereof, in an amount, per unit form, equivalent to from 300 mg to 600 mg; and netupitant-300/palonosetron-0.5.

Advantageously, said NK1-antagonist is aprepitant, in an amount per unit form of from 10 mg to 250 mg; fosaprepitant meglumine, in an amount per unit form equivalent to from 10 mg to 250 mg of aprepitant; or rolapitant, in an amount per unit form of from 15 mg to 270 mg or from 30 mg to 270 mg.

In combination with said advantageous NK1-antagonist in said pharmaceutical composition, said 6-propylamino-4, 5,6,7-tetrahydro-1,3-benzothiazole-2-amine may be pramipexole or a pharmaceutically acceptable salt thereof, safely administered to a patient suffering from a synucleinopathy at a daily dose equivalent to from 0.375 mg to 45 mg, advantageously from more than 4.5 mg to 45 mg, preferably from more than 6 mg to 45 mg or from 6.5 mg to 45 mg, or in some cases equivalent to from 1.5 mg to 22.5 mg, from 1.6 mg to 22.5 mg, from 1.625 mg to 22.5 mg, from 3 mg to 22.5 mg, from more than 4.5 mg to 22.5 mg, from 4.8 mg to 22.5 mg, from more than 6 mg to 22.5 mg or from 6.5 mg to 22.5 mg of pramipexole dihydrochloride monohydrate. Normally, said daily dose is equivalent to from 0.375 mg to 40-42 mg, advantageously from more than 4.5 mg to 40-42 mg, preferably from more than 6 mg to 40-42 mg or from 6.5 mg to 40-42 mg, or in some cases equivalent to from 1.5 mg to 20-21 mg, from 1.6 mg to 20-21 mg, from 1.625 mg to 20-21 mg, from 3 mg to 20-21 mg, from more than 4.5 mg to 20-21 mg, from 4.8 mg to 20-21 mg, from more than 6 mg to 20-21 mg or from 6.5 mg to 20-21 mg of pramipexole dihydrochloride monohydrate.

Said advantageous NK1-antagonist in said pharmaceutical composition may also be destined to the treatment of a synucleinopathy with the 6-propylamino-4,5,6,7-tetrahydro-1,3-benzothiazole-2-amine as a (R)/(S)-mixture, at a daily dose of from 150 mg to 3000 mg, normally from 300 mg to 3000 mg, said daily dose being inclusive of a (S)-enantiomer daily dose equivalent to from 0.375 mg to 45 mg, preferably from more than 6 mg to 45 mg or from 6.5 mg to 45 mg, normally from 0.375 mg to 40-42 mg, preferably from more than 6 mg to 40-42 mg or from 6.5 mg to 40-42 mg of pramipexole dihydrochloride monohydrate, said 6-propylamino-4,5,6,7-tetrahydro-1,3-benzothiazole-2-amine also being in a pharmaceutical in dosage unit form, in admixture with a pharmaceutical carrier or vehicle.

Said advantageous NK1-antagonist in said pharmaceutical composition may further be destined to the treatment of a synucleinopathy with the 6-propylamino-4,5,6,7-tetrahydro-1,3-benzothiazole-2-amine as the racemate, at a daily dose equivalent to from 0.75 mg to 90 mg, preferably from more than 12 mg to 90 mg or from 13 mg to 90, normally from 0.75 mg to 80 mg, preferably from more than 12 mg to 80 mg or from 13 mg to 80 mg of pramipexole dihydrochloride monohydrate, said 6-propylamino-4,5,6,7-tetrahydro-1,3-benzothiazole-2-amine also being in a pharmaceutical in dosage unit form, in admixture with a pharmaceutical carrier or vehicle For their administration for the treatment of synucleinopathies, the NK1-antagonist and the 6-propylamino-4,5,6,7-tetrahydro-1,3-benzothiazole-2-amine are each formulated in a pharmaceutical composition in admixture with a pharmaceutical carrier or vehicle.

In the treatment of synucleinopathies, the NK1-antagonist and the 6-propylamino-4,5,6,7-tetrahydro-1,3-benzothiazole-2-amine are used in combination and the two active components may be co-administered simultaneously or sequentially, or in a fixed dose combination including a pharmaceutical composition comprising the NK1-antagonist and 6-propylamino-4,5,6,7-tetrahydro-1,3-benzothiazole-2-amine, in admixture with a pharmaceutically acceptable carrier or vehicle.

The NK1-antagonist Component (a) and the 6-propylamino-4,5,6,7-tetrahydro-1,3-benzothiazole-2-amine Component (b) can be administered separately or together in any conventional oral or parenteral dosage unit form such as capsule, tablet, powder, cachet, suspension, solution, or transdermal device.

In the case of separate (concurrent or sequential) administration of said NK1-antagonist, in an effective amount per unit form, and of said 6-propylamino-4,5,6,7-tetrahydro-1,3-benzothiazole-2-amine, in an effective amount per unit form, each of them can be packaged in a kit comprising said NK1-antagonist, in admixture with a pharmaceutical carrier or vehicle, in a container; and said 6-propylamino-4,5,6,7-tetrahydro-1,3-benzothiazole-2-amine, preferably pramipexole, in admixture with a pharmaceutical carrier or vehicle, in another, separate container.

For their concurrent administration for the treatment of synucleinopathies, said NK1-antagonist and said 6-propylamino-4,5,6,7-tetrahydro-1,3-benzothiazole-2-amine or a pharmaceutically acceptable salt or solvate thereof may also be formulated together in fixed-dose combination consisting of a pharmaceutical composition comprising said NK1-antagonist and said 6-propylamino-4,5,6,7-tetrahydro-1,3-benzothiazole-2-amine, in admixture with a pharmaceutical carrier or vehicle.

The fixed-dose combinations assure the safe, concurrent administration of the NK1-antagonist and of the 6-propylamino-4,5,6,7-tetrahydro-1,3-benzothiazole-2-amine.

As set forth above, the amount per unit form of the NK1-antagonist is at least as high as the dose approved for the prevention or treatment of postoperative nausea and vomiting or for the prevention of chemotherapy-induced nausea and vomiting and may be up to 6 times said dose.

According to a fourth aspect, the invention provides a pharmaceutical fixed-dose combination consisting of a pharmaceutical composition in dosage unit form comprising as an active ingredient, an effective amount of a NK1-antagonist, as shown above, or of one of its pharmaceutically acceptable salts and solvates, as Component (a); and, as a second active ingredient, an effective amount per unit form of 6-propylamino-4,5,6,7-tetrahydro-1,3-benzothiazole-2-amine, as Component (b), in admixture with a pharmaceutical carrier or vehicle.

Advantageously, said NK1-antagonist Component (a) is in an amount per unit form that is at least as high as the dose approved for the prevention and treatment of postoperative nausea and vomiting or for the prevention of chemotherapy-induced nausea and vomiting.

The NK1-antagonist Component (a) is present in said fixed-dose combination in an amount per unit form of from 1 µg to 600 mg, normally from 1 mg to 600 mg or from 1 mg to 300 mg; and the 6-propylamino-4,5,6,7-tetrahydro-1,3-benzothiazole-2-amine Component (b) is present in said fixed-dose combination in an amount per unit form of from 0.125 mg to 3000 mg.

In particular, according to this fourth aspect, the invention provides a pharmaceutical composition in dosage unit form which comprises
(a) a NK1-antagonist, in an amount per unit form of from 1 µg to 600 mg; and (b) a 6-propylamino-4,5,6,7-tetrahydro-1,3-benzothiazole-2-amine selected from the group consisting of pramipexole or a pharmaceutically acceptable salt thereof, in an amount equivalent to from 0.125 mg to 45 mg, preferably from 0.125 mg to 40-42-42 mg of pramipexole dihydrochloride monohydrate; the racemate or a pharmaceutically acceptable salt thereof, in an amount per unit form equivalent to from 0.25 mg to 90 mg, preferably from 0.25 mg to 80 mg of pramipexole dihydrochloride monohydrate; and a (R)/(S)-mixture, in an amount per unit form of from 50 mg to 3000 mg, inclusive of a (S)-enantiomer amount per unit form equivalent to from 0.125 mg to 45 mg, preferably from 0.125 mg to 40-42 mg of pramipexole dihydrochloride monohydrate,
in admixture with a pharmaceutical carrier or vehicle.

Preferably, the amount/unit form of the NK1-antagonist is at least as high as the pediatric or adult dose shown effective or approved for the prevention or treatment of postoperative nausea and vomiting or for the prevention of the chemotherapy-induced nausea and vomiting and may be up to 6 times said dose.

According to a first embodiment, the NK1-antagonist Component (a) is aprepitant, in an amount per IR unit form of from 10 mg to 125 mg or rolapitant, in a dose per unit form of from 15 mg to 270 mg and the 6-propylamino-4,5,6,7-tetrahydro-1,3-benzothiazole-2-amine is present in said composition in an amount per IR-unit form of from 0.125 mg to 1500 mg (in said fixed-dose combination with the NK1-antagonist).

Preferably, in said pharmaceutical composition, said NK1-antagonist Component (a) is aprepitant, in an IR dose ranging from 10 mg to 125 mg in an IR formulation.

The dose of the 6-propylamino-4,5,6,7-tetrahydro-1,3-benzothiazole-2-amine Component (b) per IR-unit form normally is from 0.125 mg to 1500 mg, advantageously from 1.6 mg to 1500 mg preferably from 1.625 mg to 1500 mg, depending on safety and tolerability (in combination with the NK1-antagonist Component (a)).

Said dose of the 6-propylamino-4,5,6,7-tetrahydro-1,3-benzothiazole-2-amine per IR-unit form will normally range from 1.5 mg to 1500 mg depending on safety and tolerability (in combination with the NK1-antagonist).

According to this first embodiment, if said 6-propylamino-4,5,6,7-tetrahydro-1,3-benzothiazole-2-amine Component (b) of the fixed-dose combination is pramipexole or a pharmaceutically acceptable salt or solvate thereof, the dose-range per IR-unit form will be equivalent to from 0.125 mg to 30 mg, normally from 0.125 mg to 22.5 mg, from 0.125 mg to 11.25 mg, preferably from 0.125 mg to 30 mg or from 0.125 mg to 20-21 mg, normally from 0.125 mg to 10 mg of pramipexole dihydrochloride monohydrate, depending on safety and tolerability (in combination with the NK1-antagonist). Normally, if said 6-propylamino-4,5,6,7-tetrahydro-1,3-benzothiazole-2-amine is pramipexole dihydrochloride monohydrate in IR formulation, the dose range is from 0.125 mg to 30 mg or from 0.125 mg to 20-21 mg, normally from 0.125 mg to 10 mg, per IR-unit form, depending on safety and tolerability (in combination with the NK1-antagonist). If the NK1-antagonist is aprepitant, the aprepitant dose per IR unit form, in combination with pramipexole dihydrochloride monohydrate, will be from 10 mg to 125 mg of aprepitant.

If said 6-propylamino-4,5,6,7-tetrahydro-1,3-benzothiazole-2-amine Component (b) of the fixed-dose combination is the racemate, said dose-range per IR-unit will be from 0.25 mg to 45 mg, preferably from 0.25 mg to 40-42 mg, thus comprising the (S)-enantiomer in an amount per unit form equivalent to from 0.125 mg to 22.5 mg, preferably from 0.125 mg to 20-21 mg of pramipexole dihydrochloride monohydrate, and (R)-6-propylamino-4,5,6,7-tetrahydro-1,3-benzothiazole-2-amine, in an amount per unit form equivalent to from 0.125 mg to 20-21 mg of pramipexole dihydrochloride monohydrate.

If said 6-propylamino-4,5,6,7-tetrahydro-1,3-benzothiazole-2-amine Component (b) of the fixed-dose combination is a (R)/(S)-mixture in an IR formulation, said dose-range per IR-unit will be from 50 mg to 1500 mg, inclusive of a (S)-enantiomer amount per unit form equivalent to from 0.125 mg to 22.5 mg, preferably from 0.125 mg to 20-21 mg of pramipexole dihydrochloride monohydrate, thus comprising said (S)-enantiomer in an amount per unit form equivalent to from 0.125 mg to 22.5 mg, preferably from 0.125 mg to 20-21 mg of pramipexole dihydrochloride monohydrate, and (R)-6-propylamino-4,5,6,7-tetrahydro-1,3-benzothiazole-2-amine, in an amount per unit form equivalent to from 50 mg to 1500 mg (minus 0.125 mg to 22.5 mg, preferably 0.125 mg to 20-21 mg) of pramipexole dihydrochloride monohydrate.

The dose of the 6-propylamino-4,5,6,7-tetrahydro-1,3-benzothiazole-2-amine Component (b) per ER-unit form normally is from 0.375 mg to 3000 mg, advantageously from more than 4.5 mg to 3000 mg preferably from 6.5 mg to 3000 mg, depending on safety and tolerability (in combination with the NK1-antagonist Component (a)).

If said 6-propylamino-4,5,6,7-tetrahydro-1,3-benzothiazole-2-amine Component (b) of the fixed-dose combination is pramipexole or a pharmaceutically acceptable salt or solvate thereof, in an ER formulation, including slow-release compositions and transdermal therapeutic systems such as transdermal patches, its amount per unit form will be equivalent to a range of from 1.5 mg to 45 mg, from 3 mg to 45 mg, or from 3 mg to 22.5 mg, preferably from 1.5 mg to 40-42 mg, from 3 mg to 40-42 mg or from 3 mg to 20-21 mg of pramipexole dihydrochloride monohydrate depending on the tolerability (in combination with the NK1-antagonist). In particular, if said 6-propylamino-4,5,6,7-tetrahydro-1,3-benzothiazole-2-amine is pramipexole dihydrochloride monohydrate, the dose-range/unit form will be from 1.5 mg to 45 mg, normally from 3 mg to 45 mg, or from 3 mg to 22.5 mg, preferably from 1.5 mg to 40-42 mg, normally from 3 mg to 40-42 mg or from 3 mg to 20-21 mg.

If said 6-propylamino-4,5,6,7-tetrahydro-1,3-benzothiazole-2-amine Component (b) of the fixed-dose combination is a (R)/(S)-mixture in an ER formulation, including slow-release compositions and transdermal therapeutic systems such as transdermal patches, said dose-range/ER-unit will be from 150 mg to 3000 mg or from 300 mg to 3000 mg, inclusive of a (S)-enantiomer amount per unit form equivalent to from 3 mg to 45 mg, preferably from more than 4.5 mg to 45 mg, from more than 6 mg to 45 or from 6.5 mg to 45 mg, normally from 3 mg to 40-42 mg, preferably from more than 4.5 mg to 40-42 mg, from more than 6 mg to 40-42 or from 6.5 mg to 40-42 mg of pramipexole dihydrochloride monohydrate, depending on the tolerability (in combination with the NK1-antagonist), thus comprising, for example in the 3-40-42 mg-dose range case, said (S)-enantiomer in an amount per unit form equivalent to from 3 mg to 45 mg, preferably from 3 mg to 40-42 mg of pramipexole dihydrochloride monohydrate, and (R)-6-propylamino-4,5,6,7-tetrahydro-1,3-benzothiazole-2-amine, in an amount per unit form equivalent to from 150 mg to 3000 mg or from 300 mg to 3000 mg (minus 3 mg to 45 mg, preferably 3 mg to 40-42 mg) of pramipexole dihydrochloride monohydrate.

If said 6-propylamino-4,5,6,7-tetrahydro-1,3-benzothiazole-2-amine Component (b) of the fixed-dose combination is the racemate, said dose-range per ER-unit form will be equivalent to a range selected from the group consisting of from 6 mg to 90 mg, preferably from more than 9 mg to 90 mg, from more than 12 mg to 90 or from 13 mg to 90 mg, normally from 6 mg to 80 mg, preferably from more than 9 mg to 80 mg, from more than 12 mg to 80 or from 13 mg to 80 mg of pramipexole dihydrochloride monohydrate, depending on the tolerability, in combination with the NK1-antagonist, thus comprising, for example in the 6-80 mg-dose range case, an (S)-enantiomer amount per unit form for example equivalent to from 3 mg to 45 mg, preferably from 3 mg to 40-42 mg of pramipexole dihydrochloride monohydrate, and (R)-6-propylamino-4,5,6,7-tetrahydro-1,3-benzothiazole-2-amine, in an amount per unit form equivalent to from 3 mg to 45 mg, preferably from 3 mg to 40-42 mg of pramipexole dihydrochloride monohydrate.

Specific amounts per unit form of the NK1-antagonist and, respectively, of the 6-propylamino-4,5,6,7-tetrahydro-1,3-benzothiazole-2-amine active ingredients, in particular the amounts per unit form sub-ranges of said Component (a) and of said Component (b) are illustrated in "The NK1-antagonist Component (a)" and in "The 6-propylamino-4,5,6,7-tetrahydro-1,3-benzothiazole-2-amine Component (b)" sections.

If the NK1-antagonist is aprepitant, the dose/unit form will range from 10 mg to 250 mg.

If the NK1-antagonist is rolapitant, the dose per unit form in combination with 6-propylamino-4,5,6,7-tetrahydro-1,3-benzothiazole-2-amine, at the above doses/unit form, will range from 30 mg to 270 mg.

The Formulations

For the intended use in the treatment of synucleinopathies in combination with 6-propylamino-4,5,6,7-tetrahydro-1,3-benzothiazole-2-amine, the NK1-antagonist is formulated in a pharmaceutical composition, wherein said NK1-antagonist is in admixture with a pharmaceutical carrier or vehicle. For said treatment, also the 6-propylamino-4,5,6,7-tetrahydro-1,3-benzothiazole-2-amine is formulated in a pharmaceutical composition, wherein said 6-propylamino-4,5,6,7-tetrahydro-1,3-benzothiazole-2-amine is in admixture with a pharmaceutical carrier or vehicle.

In the pharmaceutical compositions of the present invention for oral, subcutaneous, intravenous, transdermal or topical administration, the active ingredients are preferably administered in the form of dosage units, in admixture with the classic pharmaceutical carriers or vehicles, as set forth above.

The dosage, i.e. the amount of active ingredient in a single dose (amount per unit form) to be administered to the patient, can vary widely depending on the age, weight, and the health condition of the patient. This dosage includes the administration of a dose from 1 µg to 600 mg, normally from 1 mg to 600 mg or from 1 mg to 300 mg, according to the potency of each NK1-antagonist and the age of the patient, and an amount of 6-propylamino-4,5,6,7-tetrahydro-1,3-benzothiazole-2-amine that is equivalent to from 0.125 mg to 45 mg, preferably from 0.125 mg to 40-42 mg of pramipexole dihydrochloride monohydrate, according to the age of the patient, from one to three times a day by intravenous, subcutaneous, oral, or transcutaneous administration, according to the strength of the doses of the each of the active ingredients.

If the NK1-antagonist is aprepitant, said dosage ranges from 10 mg to 250 mg; and, if the 6-propylamino-4,5,6,7-tetrahydro-1,3-benzothiazole-2-amine is pramipexole dihydrochloride monohydrate, said dosage ranges from 0.125 mg to 45 mg, preferably from 0.125 mg to 40-42 mg.

If the NK1-antagonist is rolapitant, said dosage ranges from 15 mg to 270 mg; and, if the 6-propylamino-4,5,6,7-tetrahydro-1,3-benzothiazole-2-amine is pramipexole dihydrochloride monohydrate, said dosage ranges from 0.125 mg to 45 mg, preferably from 0.125 mg to 40-42 mg.

The pharmaceutical compositions of the present invention are in unit form formulated with the classic excipients suitable for different ways of administration, as described above. Said unit forms are manufactured according to conventional technologies allowing, for example, the formulation of the NK1-antagonist in an IR-form and of pramipexole dihydrochloride monohydrate in ER-form in the same unit-form. Particularly advantageous are the formulations in the form of tablets, multi-score tablets, multi-layer tablets, coated tables, orally disintegrating tablets, extended release tablets, hard or soft capsules, multi-compartment capsules, extended-release capsules, patches for transdermal administration, liquid oral solutions, syrups or suspensions in a predetermined unit form, and vials for the intravenous or subcutaneous administration.

The pharmaceutical compositions may be formulated in oral unit forms such as tablets or gelatin capsules wherein the 6-propylamino-4,5,6,7-tetrahydro-1,3-benzothiazole-2-amine or the NK1-antagonist or both the active ingredients are in admixture with a carrier or vehicle that may include a diluent, such as cellulose, dextrose, lactose, mannitol, sorbitol or sucrose; a lubricant, such as, acid, calcium or magnesium stearate, polyethylene glycol, silica, or talc; and if needed, a binder such as magnesium aluminum silicate, gelatin, methylcellulose, sodium carboxymethylcellulose, or polyvinylpyrrolidone.

Said oral unit forms may be tablets coated with sucrose or with various polymers for an immediate release; or, alternatively, the tablets can be manufactured by using carriers such as acrylic and methacrylic acid polymers and copolymers; cellulose derivatives such as hydroxypropylethylcellulose; or other appropriate materials, to have a prolonged or delayed activity by progressively releasing a predetermined quantity of NK1-antagonist, or of 6-propylamino-4,5,6,7-tetrahydro-1,3-benzothiazole-2-amine, or of both the active ingredients. The oral formulations can also be in form of capsules allowing the extended release of the NK1-antagonist, or of the 6-propylamino-4,5,6,7-tetrahydro-1,3-benzothiazole-2-amine, or of both the active ingredients.

Said oral unit forms may also be tablets or capsules wherein one of the active ingredient is in an IR-formulation and the other one is in an ER-formulation. For example said unit form comprises aprepitant or rolapitant in an IR-formulation and pramipexole dihydrochloride monohydrate in an ER-formulation, each at the amount per unit form as described above.

The pharmaceutical compositions may also be formulated in TTS, such as a patch formulation wherein the active ingredient or the mixture of the active ingredients may comprise adjuvants such as D-sorbitol, gelatin, kaolin, methyl paraben, polysorbate 80, propylene glycol, propyl paraben, povidone, sodium carboxymethylcellulose, sodium polyacrylate, tartaric acid, titanium dioxide, and purified water. A patch formulation may also contain skin permeability enhancer such as lactate esters (e.g., lauryl lactate), triacetin or diethylene glycol monoethyl ether.

In the above pharmaceutical compositions, the preferred NK1-antagonist active ingredient is aprepitant, fosaprepitant, rolapitant or netupitant-300/pslonosetron-0.5, and the preferred 6-propylamino-4,5,6,7-tetrahydro-1,3-benzothiazole-2-amine active ingredient is pramipexole base or its dihydrochloride monohydrate.

Thus, for example, a pharmaceutical composition according to the present invention to be chronically administered in combination with 6-propylamino-4,5,6,7-tetrahydro-1,3-benzothiazole-2-amine, preferably pramipexole dihydrochloride monohydrate, in an amount per unit form of from 0.125 mg to 30 mg or from 1.5 mg to 22.5 mg, normally from 1.5 mg to 11.25 mg, preferably from 0.125 mg to 20 mg, normally from 1.5 mg to 10 mg, in IR-formulation, or in an amount per unit form of from 1.5 mg to 45 mg, preferably from 1.5 mg to 40-42 mg in an ER-formulation, to be administered at a daily dose of from 1.5 mg to 45 mg, normally from 3 mg to 22.5 mg from 1.5 mg to 40-42 mg, normally from 3 mg to 20-21 mg, preferably comprise aprepitant, in an amount per unit form of from 10 mg to 250 mg, in a formulation to be administered once a day; or rolapitant, in an amount per unit form of from 15 mg to 270 mg, in a formulation to be administered once a day.

In the case of pediatric or obese patients, the NK1-antagonist daily dose may be decided on the basis of the body weight. Thus, for example, aprepitant may be administered at a daily dose of 0.16 mg/kg to 4.2 mg/kg and rolapitant may be administered at a daily dose of 0.25 mg/kg to 4.5 mg/kg.

EXAMPLES

Example 1

The ability of the NK1-antagonists for preventing the adverse effects of 6-propylamino-4,5,6,7-tetrahydro-1,3-benzothiazole-2-amine in humans was tested.

A Phase I study was conducted in subjects receiving oral doses of pramipexole dihydrochloride monohydrate ("pramipexole") with or without aprepitant. The study was a single center, single-blind, placebo-controlled study.

The objective of the study was to demonstrate that aprepitant could safely attenuate the gastro-intestinal side effects of pramipexole given in therapeutic and even in supratherapeutic doses.

To be enrolled in the study, participants (aged 18 to 60 years of age) were required to be in good health, to refrain from consuming xanthine, quinine and caffeine containing beverages, and to refrain from prolonged intensive physical exercise during the study conduct. All subjects signed an informed consent form indicating that they understood the purpose of and procedures required for the study and that they were willing to participate in the study and comply with the study procedures and restrictions. The key criteria for exclusion of a subject from enrollment in the study were as follows:

1. Any clinically relevant acute or chronic disease which could interfere with the subjects' safety during the trial, exposes them to undue risk, or interfere with the study objectives.
2. History or presence of gastrointestinal, hepatic, or renal disease or other condition known to interfere with the absorption, distribution, metabolism or excretion of drugs.
3. History of substance abuse, known drug addiction, or positive test for drugs of abuse or alcohol.
4. History of drug or other significant allergy.
5. ECG changes including QT interval prolongation and congenital long QT syndrome. Electrolyte abnormalities (e.g., hypokalemia or hypomagnesemia), congestive heart failure, bradyarrhythmias or other conditions that lead to QT prolongation.
6. Treatment with centrally active drugs or those affecting peripheral cholinergic transmission within 3 months of study entry.
7. Smokers (except subjects who stopped smoking 1 year or more before enrollment in the Study).
8. Excessive daily consumption of xanthines containing drinks (i.e. >500 mg/day of caffeine).
9. Intake of an investigational drug within 30 days of study entry.

Following enrollment in the study, participants received single increasing oral doses of pramipexole (ranging from 1.25 mg to 20 mg) plus placebo, given once daily in the morning. Once a subject had reached first intolerable dose (FID-1), upward dose escalation was discontinued. First intolerable dose (FID) was defined as:
 one episode of vomiting; or
 two episodes of retching; or
 one episode of severe nausea.

Following a wash-out period, participants received pramipexole with aprepitant, (in doses of aprepitant from 10 mg to 250 mg, starting at 10 mg and increasing to 250 mg as necessary to delay onset of intolerability), and subjects continued to receive aprepitant with increasing doses of pramipexole until subjects reached a second intolerable dose (FID-2). On each study day, subjects were followed up for up to 8 hours for tolerability and safety.

Results showed that the co-administration of aprepitant with pramipexole allowed tolerable increases in the dose of pramipexole resulting in toleration of higher pramipexole doses than if pramipexole had been given alone.

Example 2

A Phase I study was conducted in subjects receiving a single oral dose of pramipexole dihydrochloride monohydrate ("pramipexole") with or without a single oral dose of aprepitant. The study was a single center, single-blind study.

The objective of the study was to demonstrate that aprepitant could safely attenuate the gastro-intestinal side effects of pramipexole given in doses equivalent or higher than those approved in the treatment of Parkinson's Disease or shown in clinical trials to be effective in the treatment of depression.

To be enrolled in the study, participants the following inclusion/exclusion key criteria:

Key Inclusion Criteria
1. Male and female subjects aged 20-45 years old both ages included.
2. Females of childbearing potential must agree to be abstinent or else use any two of the following medically acceptable forms of contraception from the Screening Period through 14 days after the study Exit Visit: condom with spermicidal jelly, diaphragm or cervical cap with spermicidal jelly, or intrauterine device (IUD). A female whose male partner has had a vasectomy must agree to use one additional form of medically acceptable contraception. Subjects must agree to practice the above birth control methods for 14 days after the final visit as a safety precaution.
3. Females of non-childbearing potential, defined as surgically sterile (status post-hysterectomy, bilateral oophorectomy, or bilateral tubal ligation) or post-menopausal for at least 12 months, do not require contraception during the study. The reason must be documented in the source documents.
4. Males with female partners of childbearing potential must agree to use a highly effective, medically acceptable form of contraception from the Screening Period through 14 days after the study Exit Visit. Males with female partners of childbearing potential who themselves are surgically sterile (status post vasectomy) must agree to use condoms with spermicide over the same period of time. Male subjects must agree to practice the above birth control methods for 14 days after the final visit as a safety precaution.
5. Subjects must be in good health as determined by their medical history including personal and family psychiatric history and results of physical examination, electrocardiogram (ECG), vital signs, and laboratory tests. A subject with a medical abnormality may be included only if the investigator or designee considers that the abnormality will not introduce significant additional risk to the subject's health or interfere with study objectives.
6. Subjects must be able to clearly and reliably communicate changes in their medical condition.
7. Subjects with a body mass index (BMI) between 19.0 and 32.0 kg/m² (both inclusive).
8. Subjects able to swallow multiple pills or capsules simultaneously.
9. Subjects must have signed an informed consent form indicating that they understand the purpose of and procedures required for the study and are willing to participate in the study and comply with the study procedures and restrictions.

Key Exclusion Criteria:
The criteria for exclusion of a subject from enrollment in the study were as follows:
1. Any clinically relevant acute or chronic diseases which could interfere with the subjects' safety during the trial, expose them to undue risk, or interfere with the study objectives.
2. History or presence of gastrointestinal, hepatic, or renal disease or other condition known to interfere with the absorption, distribution, metabolism or excretion of the study drugs.
3. History of substance abuse, known drug addiction, or positive test for drugs of abuse or alcohol.
4. History of drug or other significant allergy.
5. Known hypersensitivity to pramipexole, or to ondansetron or similar serotonin receptor antagonists, or to aprepitant or similar Substance P/NK1 receptor antagonists.
5. History of and/or current QT interval prolongation, congenital long QT syndrome, electrolyte abnormalities (e.g., hypokalemia or hypomagnesemia), congestive heart failure, bradyarrhythmias or other medicinal products that lead to QT prolongation or 1st degree AV block at Screening, Day −1, or pre-dose, ≥450 QTcF for males and ≥470 QTcF for females.
7. Treatment with centrally active drugs or antiemetics, within 1 months of study entry.
8. Tobacco or nicotine users (except subjects who stopped using tobacco or nicotine 1 year or more before enrollment in the study).
9. Excessive daily consumption of xanthines containing drinks (i.e. >500 mg/day of caffeine).
10. Subjects unwilling to curtail prolonged intensive physical exercise during the study conduct (from the Screening visit until the last dose of study drug).

11. Positive test result for hepatitis B surface antigen, hepatitis C antibody.
12. Positive test result for HIV 1 or 2 serology.
13. Likely to need any medical or dental treatment during the study period.
14. Use of any prescription or over-the-counter medication within 14 days prior to admission on Day-1. In addition any medications with central effects are prohibited for a period equal to 5 times the drug half-life prior to admission (Day −1), should this period be longer than 14 days.
15. Subjects unlikely to co-operate during the study, and/or be questionably compliant in the opinion of the investigator.
16. Subjects unable to be contacted in case of an emergency.
17. Intake of an investigational drug within 30 days of study entry.
18. Show evidence of suicidal ideation within the last 6 months as assessed by the C-SSRS (Columbia Suicide Severity Rating Scale) at Screening.

Following enrollment in the study, participants received single increasing oral doses of pramipexole given once daily in the morning (Period 1 of the study). The starting dose of pramipexole was 0.5 mg and the dose was increased daily by 0.5 mg increments. Once a subject had reached his/her first intolerable dose (FID-1), upward dose escalation was discontinued. First intolerable dose (FID) was defined as:
One (1) episode of vomiting; or
Two (2) episodes of retching, or
One (1) episode of severe nausea (Grade 3; defined as nausea interfering with activities of daily living or inadequate oral caloric or fluid intake; tube feeding, total parenteral nutrition or hospitalization indicated) lasting more than 1 hour, or
Three (3) consecutive episodes at every 4 hour ratings of moderate nausea (Grade 2; defined as subjectively symptomatic, but not interfering with activities of daily living), or
One (1) episode of moderate diarrhea (Grade 2; defined as 4-6 stools more than at baseline).

When a subject reached FID-1 on pramipexole alone, the subject was washed out for at least 5 days, and then entered Period 2 of the study during which the subject received single daily oral doses of pramipexole starting at 0.5 mg and titrated upward by 0.5 mg increments, together with oral aprepitant (80 mg) until subjects again reached an intolerable dose defined as above. The FID on oral pramipexole plus oral aprepitant was referred to as FID-2.

If a subject reached FID-2 during Period 2 at the same or lower dose than FID-1, and providing the investigator judged there were no safety issues and the subject was consenting, the subject received the same dose of pramipexole as the FID-2 dose together with a higher dose of oral aprepitant (120 mg) on the next day and the protocol specified that said subject should continue with the remainder of the dose titration with the higher dose of oral aprepitant (120 mg) until they reach the intolerable dose (FID2+). All other provisions of the protocol remained unchanged. Assessments were the same as those planned for the dose escalation day.

On each study day, subjects were followed up for up to 8 hours following drug administration for AEs, vital signs, ECGs. In addition, a laboratory panel was taken at screening and at the end of the study.

Four subjects were enrolled in the study. The following Table 1 summarizes the demographic characteristics of the subjects.

TABLE 1

Demographic Characteristics of Subjects Enrolled in the Study

| Subject ID | Gender | Age (years) | Baseline Weight (kg) |
|---|---|---|---|
| 1001 (019) | Female | 40 | 76.4 kg |
| 1006 (001) | Male | 41 | 99.1 kg |
| 1007 (004) | Male | 38 | 64.9 kg |
| 1008 (008) | Male | 39 | 81.8 kg |

All subjects reached FID-1 (pramipexole alone) during the study. The dose limiting toxicity was gastro-intestinal adverse events in all 4 subjects. During Period 2 of the study, all 4 subjects tolerated the maximum pramipexole dose allowed by the protocol of 6 mg and therefore none of them reached FID-2 (pramipexole with aprepitant). In other words, concomitant administration of aprepitant with pramipexole prevented the occurrence of dose-limiting gastro-intestinal adverse events associated with high doses of pramipexole. Table 2 lists for each subject the values for FID-1 (on pramipexole alone) and FID-2 (on pramipexole+aprepitant).

TABLE 2

Listing of First Intolerable Doses (FID) values

| Subject ID | FID-1 (Pramipexole alone) | FID-1 Dose Limiting Adverse Event | FID-2 Pramipexole + Aprepitant |
|---|---|---|---|
| 1001 | 2.5 mg | GI issues | >6.0 mg |
| 1006 | 0.5 mg | Moderate nausea | >6.0 mg |
| 1007 | 4.5 mg | Severe nausea | >6.0 mg |
| 1008 | 1.5 mg | Vomiting | >6.0 mg |

As shown in the following Table 3, the Maximum Tolerated Dose (MTD) during Period 2 was higher than MTD during Period 1 in all subjects, and in 3 subjects MTD-2 was increased by more than 3-fold.

TABLE 3

Listing of Maximum Tolerated Doses (MTD)

| Subject ID | MTD-1 (Pramipexole alone) | Maximal Tolerated Dose Pramipexole + Aprepitant | MTD2/MTD1 |
|---|---|---|---|
| 1001 | 2.0 mg | ≥6.0 mg | ≥3.0 |
| 1006 | NA (not tolerated at 0.5 mg) | ≥6.0 mg | ≥12.0 |
| 1007 | 4.0 mg | ≥6.0 mg | ≥1.5 |
| 1008 | 1.0 mg | ≥6.0 mg | ≥6.0 |

MTD: Maximum Tolerated Dose

Taken together, results showed that the co-administration of aprepitant with pramipexole attenuated dose-limiting gastro-intestinal adverse effects reported with pramipexole alone, thus showing that a NK1-antagonist enables the administration to a human being of pramipexole in doses otherwise non-tolerated when administering pramipexole alone.

In conclusion, the co-administration of aprepitant with pramipexole inhibited the occurrence of gastro-intestinal AEs associated with pramipexole given alone, thus enabling doses of pramipexole to be safely and tolerably raised by more than 2-fold, thereby allowing a far greater efficacy of this drug. In particular, these results show that the protective action of a NK1-antagonist allows the safe treatment of a human with pramipexole not only within the pramipexole approved dose range but also at doses that are higher than its maximum recommended dose,

REFERENCES

Al-Mansoori et al. 2013: Al-Mansoori K M, Hasan M Y, Al-Hayani A, El-Agnaf M, "*The role of α-synuclein in neurodegenerative diseases: from molecular pathways in disease to therapeutic approaches*"; Curr. Alzheimer Res. 2013 July; 10(6): 559-568.

Chen et al. 2016 Min Chen, Weiwei Yang, Xin Li, Xuran Li, Peng Wang, Feng Yue, Hui Yang, Piu Chan, and Shun Yu; "*Age-and brain region-dependent α-synuclein oligomerization is attributed to alterations in intrinsic enzymes regulating α-synuclein phosphorylation in aging monkey brains*"; Oncotarget. 2016 Feb. 23; 7(8): 8466-8480.

Corrigan et al. 2000: Corrigan M H, Denahan A Q, Wright C E, Ragual R J, Evans D L; Corrigan M H, Denahan A Q, Wright C E, Ragual R J, Evans D; "*Comparison of pramipexole, fluoxetine, and placebo in patients with major depression*"; Depress Anxiety. 2000; 11(2):58-65.

Gardner et al 1996; Gardner C J, Armour D R, Beattie D T, Gale J D, Hawcock A B, et al. (1996) GR205171: a novel antagonist with high affinity for the tachykinin NK1 receptor, and potent broad-spectrum anti-emetic activity. Regul Pept 65: 45-53.

Inden et al. 2009: Inden M, Kitamura Y, Tamaki A, Yanagida T, Shibaike T, Yamamoto A, Takata K, Yasui H, Taira T, Ariga H, Taniguchi T; "*Neuroprotective effect of the antiparkinsonian drug pramipexole against nigrostriatal dopaminergic degeneration in rotenone-treated mice.*"; Neurochem Int. 2009 December; 55(8):760-7.

Jellinger K A 2008a: Jellinger K A, "*A critical reappraisal of current staging of Lewy-related pathology in human brain*"; Acta Neuropathol. 2008 July; 116(1): 1-16.

Jellinger K A 2008b: Jellinger K A, "*Neuropathological aspects of Alzheimer disease, Parkinson disease and frontotemporal dementia*"; Neurodegener. Dis. 2008; 5(3-4): 118-121.

Kakimura et al. 2001: Kakimura J, Kitamura Y, Takata K, Kohno Y, Nomura Y, Taniguchi T; "*Release and aggregation of cytochrome c and alpha-synuclein are inhibited by the antiparkinsonian drugs, talipexole and pramipexole*"; Eur J Pharmacol. 2001 Apr. 6; 417(1-2):59-67.

Kim et al. 2004: Kim S, Seo J H, Suh Y H, "*Alpha-synuclein, Parkinson's disease, and Alzheimer's disease*"; Parkinsonism Relat. Disord. 2004 May; 10 Suppl. 1: S9-13.

Luo et al. 2016: Luo H T, Zhang J P, Miao F; "*Effects of pramipexole treatment on the α-synuclein content in serum exosomes of Parkinson's disease patients*"; Exp Ther Med. 2016 September; 12(3):1373-1376).

Marques and Outeiro 2012: Marques O, Outeiro T F; "*Alpha-synuclein: from secretion to dysfunction and death*"; Cell Death Dis. 2012 Jul. 19; 3:e350. doi: 10.1038/cddis.2012.94.

Ono et al. 2013: Ono K, Takasaki J, Takahashi R, Ikeda T, Yamada M; "*Effects of antiparkinsonian agents on β-amyloid and α-synuclein oligomer formation in vitro*"; J Neurosci Res; 2013 October; 91(10):1371-81).

O'Regan et al. 2017: O'Regan G, deSouza R M, Balestrino R. Schapira A H: "*Glucocerebrosidase Mutations in Parkinson Disease*"; Journal of Parkinson's Disease 2017(7) 411-422-DOI 10.3233/JPD-171092 IOS Press.

Prusiner S B et al. 2015: Prusiner S B, Woerman A L, Mordes D A, Watts J C, Rampersaud R, Berry D B, Patel S, Oehler A, Lowe J K, Kravitz S N, Geschwind D H, Glidden D V, Halliday G M, Middleton L T, Gentleman S M, Grinberg L T, Giles_K, "*Evidence for α-synuclein prions causing multiple system atrophy in humans with parkinsonism*"; Proc Natl Acad Sci USA; 2015, Sep. 22; 112(38):E5308-17.

Schapira et al. 2013: Schapira A H, McDermott M P, Barone P, Comella C L, Albrecht S, Hsu H H, Massey D H, Mizuno Y, Poewe W, Rascol O, Marek K. "*Pramipexole in patients with early Parkinson's disease (PROUD): a randomised delayed-start trial*"; Lancet Neurol. 2013 August; 12(8):747-55).

Schneider et al. 1987: Schneider C S, Mierau J; "*Dopamine autoreceptor agonists: resolution and pharmacological activity of 2,6-diaminotetrahydrobenzothiazole and an aminothiazole analogue of apomorphine*"; J. Med Chem. 1987 March; 30(3):494-498.

Shi et al. 2014: Shi M, Liu C, Cook T J, Bullock K M, Zhao Y, Ginghina C, Li Y, Aro P, Dator R, He C, Hipp M J, Zabetian C P, Peskind E R, Hu S C, Quinn J F, Galasko D R, Banks W A, Zhang J; "*Plasma exosomal α-synuclein is likely CNS-derived and increased in Parkinson's disease*"; Acta Neuropathol. 2014 November; 128(5):639-50. doi: 10.1007/s00401-014-1314-y. Epub 2014 Jul. 6.

Soria et al 2017: Soria F N, Engeln M, Martinez-Vicente M, Glangetas C, Lopez-Gonzales J, Dovero S, Dehay B, Normand E, Vila M, Lopez-Gonzales M J, Favereaux A, Georges F, Lo Bianco C, Bezard E, Fernagut; "*Glucocerebrosidase deficiency in dopaminergic neurons induces microglial activation without neurodegeneration*"; Hum Mol Genet 2017 July; 26(14):2603-2615.

Stuendl A, Kunadt M, Kruse N, Bartels C, Moebius W, Danzer K M, Mollenhauer B, Schneider A; "*Induction of alpha-synuclein in aggregate formation by CSF exosomes from patients with Parkinson's disease and dementia with Lewy bodies*" Brain 2016, 139; 481-494.

The invention claimed is:

1. A method for treating a synucleinopathy in a patient, which comprises administering to said patient in need of said treatment an effective daily dose of a NK1-antagonist in combination with an effective daily dose of 6-propylamino-4,5,6,7-tetrahydro-1,3-benzothiazole-2-amine.

2. The method of claim 1, wherein said NK1-antagonist effective daily dose is from 1 µg to 600 mg.

3. The method of claim 1, wherein said NK1-antagonist effective daily dose is from 1 mg to 600 mg.

4. The method of claim 1, wherein said NK1-antagonist is aprepitant or a pharmaceutically acceptable salt or solvate thereof.

5. The method of claim 1, wherein said NK1-antagonist is rolapitant or a pharmaceutically acceptable salt or solvate thereof.

6. The method of claim 1, wherein said NK1-antagonist is aprepitant and said 6-propylamino-4,5,6,7-tetrahydro-1,3-benzothiazole-2-amine is pramipexole dihydrochloride monohydrate.

7. The method of claim 1, wherein said NK1-antagonist is aprepitant, at an effective daily dose of from 10 mg to 250 mg and said 6-propylamino-4,5,6,7-tetrahydro-1,3-benzothiazole-2-amine is pramipexole dihydrochloride monohydrate, at an effective daily dose of from 1.5 mg to 45 mg.

8. The method of claim 1, wherein said NK1-antagonist and said 6-propylamino-4,5,6,7-tetrahydro-1,3-benzothiazole-2-amine are each formulated in a pharmaceutical composition in dosage unit form comprising, respectively, said NK1-antagonist and said 6-propylamino-4,5,6,7-tetrahydro-1,3-benzothiazole-2-amine, each in admixture with a pharmaceutical carrier or vehicle.

9. The method of claim 1, wherein said NK1-antagonist and said 6-propylamino-4,5,6,7-tetrahydro-1,3-benzothiazole-2-amine are each formulated in a pharmaceutical composition in dosage unit form comprising, respectively,
said NK1-antagonist in an amount per unit form of from 1 µg to 600 mg; and,
said 6-propylamino-4,5,6,7-tetrahydro-1,3-benzothiazole-2-amine in an amount per unit of from 0.125 mg to 3000 mg,
each in admixture with a pharmaceutical carrier or vehicle.

10. The method of claim 1, wherein said NK1-antagonist and said 6-propylamino-4,5,6,7-tetrahydro-1,3-benzothiazole-2-amine are each formulated in a pharmaceutical composition in dosage unit form comprising, respectively, said NK1-antagonist in an amount per unit form of from 1 mg to 600 mg, and said 6-propylamino-4,5,6,7-tetrahydro-1,3-benzothiazole-2-amine is pramipexole dihydrochloride monohydrate in an amount per unit form of from more than 4.5 mg to 45 mg.

11. The method of claim 10, wherein said 6-propylamino-4,5,6,7-tetrahydro-1,3-benzothiazole-2-amine is pramipexole dihydrochloride monohydrate in an amount per unit form of from more than 6 mg to 45 mg.

12. The method of claim 10, wherein said 6-propylamino-4,5,6,7-tetrahydro-1,3-benzothiazole-2-amine is pramipexole dihydrochloride monohydrate in an amount per unit form of from 6.5 mg to 45 mg.

13. The method of claim 1, wherein said NK1-antagonist and said 6-propylamino-4,5,6,7-tetrahydro-1,3-benzothiazole-2-amine are co-formulated in a pharmaceutical composition in dosage unit form comprising said NK1-antagonist, in an amount per unit form of from 1 µg to 600 mg, and said 6-propylamino-4,5,6,7-tetrahydro-1,3-benzothiazole-2-amine, in an amount per unit form of from 0.125 mg to 3000 mg, in admixture with a pharmaceutical carrier or vehicle.

14. The method of claim 1, wherein said NK1-antagonist and said 6-propylamino-4,5,6,7-tetrahydro-1,3-benzothiazole-2-amine are co-formulated in a pharmaceutical composition in dosage unit form comprising said NK1-antagonist, in an amount per unit form of from 1 µg to 600 mg, and said 6-propylamino-4,5,6,7-tetrahydro-1,3-benzothiazole-2-amine is selected from the group consisting of pramipexole and pharmaceutically acceptable salts and solvates thereof, in an amount per unit form equivalent to from 0.125 mg to 45 mg of pramipexole dihydrochloride monohydrate, in admixture with a pharmaceutical carrier or vehicle.

15. The method of claim 14, wherein, in said composition, said 6-propylamino-4,5,6,7-tetrahydro-1,3-benzothiazole-2-amine is pramipexole dihydrochloride monohydrate in an amount per unit form of from more than 4.5 mg to 45 mg.

16. The method of claim 14, wherein, in said composition, said 6-propylamino-4,5,6,7-tetrahydro-1,3-benzothiazole-2-amine is pramipexole dihydrochloride monohydrate in an amount per unit form of from more than 6 mg to 45 mg.

17. The method of claim 14, wherein, in said composition, said NK1-antagonist is aprepitant, in an amount per unit form of from 10 mg to 250 mg; and said 6-propylamino-4,5,6,7-tetrahydro-1,3-benzothiazole-2-amine is pramipexole dihydrochloride monohydrate, in an amount per unit form of from 0.125 mg to 45 mg.

18. The method of claim 1, wherein said synucleinopathy is selected from the group consisting of Parkinson's disease, Lewy body dementia, mutations in the glucocerebrosidase gene, Alzheimer's disease, the Lewy body variant of Alzheimer's disease, multiple system atrophy, neurodegeneration with brain iron accumulation, and parkinsonian disorders associated with glucocerebrosidase (GBA) mutations.

19. A pharmaceutical composition in dosage unit form which comprises
(a) a NK1-antagonist, in an amount per unit form of from 1 µg to 600 mg; and
(b) a 6-propylamino-4,5,6,7-tetrahydro-1,3-benzothiazole-2-amine selected from the group consisting of
the racemate or a pharmaceutically acceptable salt thereof, in an amount per unit form equivalent to from 0.25 mg to 90 mg of pramipexole dihydrochloride monohydrate;
pramipexole or a pharmaceutically acceptable salt thereof, in an amount equivalent to from 0.125 mg to 45 mg of pramipexole dihydrochloride monohydrate; and
a (R)/(S)-mixture, in an amount per unit form of from 50 mg to 3000 mg, inclusive of -a (S)-enantiomer amount per unit form equivalent to from 0.125 mg to 45 mg of pramipexole dihydrochloride monohydrate,
in admixture with a pharmaceutical carrier or vehicle.

20. The composition of claim 19, wherein said 6-propylamino-4,5,6,7-tetrahydro-1,3-benzothiazole-2-amine is pramipexole or a pharmaceutically acceptable salt thereof, in an amount per unit form equivalent to from more than 4.5 mg to 45 mg of pramipexole dihydrochloride monohydrate.

21. The composition of claim 19, wherein said 6-propylamino-4,5,6,7-tetrahydro-1,3-benzothiazole-2-amine is pramipexole or a pharmaceutically acceptable salt thereof, in an amount per unit form equivalent to from more than 6 mg to 45 mg of pramipexole dihydrochloride monohydrate.

22. The composition of claim 19, wherein said 6-propylamino-4,5,6,7-tetrahydro-1,3-benzothiazole-2-amine is pramipexole or a pharmaceutically acceptable salt thereof, in an amount per unit form equivalent to from 6.5 mg to 45 mg of pramipexole dihydrochloride monohydrate.

23. The composition of claim 19, wherein said NK1-antagonist is aprepitant, in an amount per unit of from 10 mg to 250 mg; and said 6-propylamino-4,5,6,7-tetrahydro-1,3-benzothiazole-2-amine is pramipexole dihydrochloride monohydrate, in an amount per unit form of from 0.125 mg to 45 mg.

* * * * *